(12) United States Patent
Hegmann et al.

(10) Patent No.: US 8,071,181 B2
(45) Date of Patent: Dec. 6, 2011

(54) METAL NANOPARTICLE AND USE THEREOF FOR INDUCING CHIRALITY IN LIQUID CRYSTAL PHASES

(75) Inventors: Torsten Hegmann, Winnipeg (CA); Hao Qi, Winnipeg (CA)

(73) Assignee: University of Manitoba, Winnipeg, Manitoba (CA)

( * ) Notice: Subject to any disclaimer, the term of this patent is extended or adjusted under 35 U.S.C. 154(b) by 699 days.

(21) Appl. No.: 12/086,720

(22) PCT Filed: Jan. 12, 2007

(86) PCT No.: PCT/CA2007/000046
§ 371 (c)(1),
(2), (4) Date: Sep. 11, 2008

(87) PCT Pub. No.: WO2007/079585
PCT Pub. Date: Jul. 19, 2007

(65) Prior Publication Data
US 2009/0027611 A1    Jan. 29, 2009

Related U.S. Application Data

(60) Provisional application No. 60/758,201, filed on Jan. 12, 2006.

(51) Int. Cl.
*C09K 19/52*  (2006.01)
*C09K 19/58*  (2006.01)
*C09K 19/34*  (2006.01)
*C07F 1/12*   (2006.01)
*C01G 5/00*   (2006.01)
*C01G 7/00*   (2006.01)

(52) U.S. Cl. ............... 428/1.1; 252/299.01; 252/299.61; 252/299.67; 423/48; 556/113; 977/700; 977/773

(58) Field of Classification Search ............. 252/299.01, 252/299.67, 299.61; 556/113; 977/700, 977/773; 423/48; 428/1.1
See application file for complete search history.

(56) References Cited

U.S. PATENT DOCUMENTS

| 6,287,649 | B1 | 9/2001 | Fukushima et al. |
| 6,482,988 | B2 | 11/2002 | Fukushima et al. |
| 2004/0250750 | A1 | 12/2004 | Reda et al. |

FOREIGN PATENT DOCUMENTS

| CA | 2334238 A1 | 12/1999 |
| CA | 2 537 199 | 3/2005 |
| WO | 2008/0134866 A1 | 11/2008 |

OTHER PUBLICATIONS

Andrienko, et al., "Computer simulation of topological defects around a colloidal particle or droplet dispersed in a nematic host" *Phys. Rev. E*, 2001; 63(4):041701-1-041701-8.

(Continued)

*Primary Examiner* — Shean Wu
(74) *Attorney, Agent, or Firm* — Mueting Raasch & Gebhardt, P.A.

(57) ABSTRACT

The invention provides a metal nanoparticle comprising a metal and a chiral and/or thiolate group bonded to the metal. The monolayer-protected metal nanoparticle may be used as a chiral dopant in a liquid crystal. Accordingly, the invention also provides a colloidal suspension or dispersion comprising a metal nanoparticle comprising a metal and a chiral and/or thiolate group bonded to the metal, and a liquid crystal.

58 Claims, 9 Drawing Sheets

Nematic Texture (non-chiral)

Periodic Stripe Texture (local chiral domains)

OTHER PUBLICATIONS

Belser et al., "Immobilization of Rhodium Complexes at Thiolate Monolayers on Gold Surfaces: Catalytic and Structural Studies" *J. Am. Chem. Soc.*, 2005; 127:8720-8731.

Brust et al., "Synthesis of thiol-derivatised gold nanoparticles in a two-phase liquid-liquid system" *J. Chem. Soc., Chem. Commun.*, 1994; 7:801-802.

Brust et al., "Synthesis and Reactions of Functionalised Gold Nanoparticles" *J. Chem. Soc., Chem. Commun.*, 1995; 16:1655-1656.

Buda et al., "A Hausdorff chirality measure", *J.Am. Chem. Soc.*, 1992; 114(15):6006-6012.

Büttner et al. "Stability of thiol-passivated gold particles at elevated temperatures studied by X-ray photoelectron spectroscopy" *J. Phys. Chem. B*, 2005; 109(12):5464-5467.

Choo et al., "Synthesis of mixed monolayer-protected gold clusters from thiol mixtures: Variation in the tail group, chain length, and solvent" *Langmuir*, 2003; 19(20):8555-8559.

Coffey et al., "Chiral Hausdorff metrics and structural spectroscopy in a complex system" *J. Phys. A: Math. Gen.*, Mar. 1999; 32(12):2263-2284.

Dierking, *Textures of Liquid Crystals*, Willey-VCH, Weinheim, Germany, 2003, title page, copyright pages and table of contents only, 6 pgs.

dos Santos, Jr. et al., "Controlling the size and shape of gold nanoparticles in fulvic acid colloidal solutions and their optical characterization using SERS" *J. Mater. Chem.*, 2005; 15:3045-3049.

Feng et al., "Orientational defects near colloidal particles in a nematic liquid crystal" *J. Colloid Interface Sci.*, Jan. 2004; 269(1):72-78.

Friedel, "The mesomorphic states of matter" *Ann. Phys. Paris*, 1922; 18:273-474. (Publication in French and English translation translated by the Translation and Interpretation Division of the Institute of Modern Languages, Washington, D.C. English translation obtained from the University of Minnesota Library Service (ESTIS)).

Fukada et al., "Interaction between particles in a nematic liquid crystal: Numerical study using the Landau-de Gennes continuum theory" *Mol. Cryst. Liq. Cryst.*, 2005; 435:63/723-74/734.

Garzón et al., "Chirality in bare and passivated gold nanoclusters" *Phys. Rev. B*, 2002; 66(7):073403-1-073403-4.

Garzón et al., "Chirality, defects, and disorder in gold clusters" *Eur. Phys. J. D*, Jun. 2003 II; 24(1-3):105-109.

Gautier et al., "Vibrational circular dichroism of N-acetyl-L-cysteine protected gold nanoparticles" *Chem. Commun.*, Nov. 2005; 43:5393-5395.

Gu et al., "Observation of saturn-ring defects around solid microspheres in nematic liquid crystals" *Phys. Rev. Lett.*, Nov. 2000; 85(22):4719-4722.

Hu et al., "A convenient trimethylsilylthioxy-dehalogenation reaction for the preparation of functionalized thiols" *J. Org. Chem.*, 1999; 64(13):4959-4961.

Kazemekaite et al., "Synthesis and self-assembling properties on gold of 2-methyl-1,4-naphthoquinone derivatives containing ω-mercaptoalkylalkanoate groups" *Tetrahedron Letters*, Apr. 2004; 45(18):3551-3555.

Kim et al., "Size-selective synthesis of gold and platinum nanoparticles using novel liquids" *Langmuir*, 2004; 20(3):556-560.

Kossyrev et al., "Branching of colloidal chains in capillary-confined nematics" *Phys. Rev. Lett.*, Feb. 2006; 96(4):048301-1-048301-4. Epub Feb. 2, 2006.

Kuksenok et al., "Director structure around a colloid particle suspended in a nematic liquid crystal" *Phys. Rev. E*, Nov. 1996; 54(5):5198-5203.

Li et al., "Circular dichroism study of chiral biomolecules conjugated with silver nanoparticles" *Nanotechnology*, 2004; 15:S660-S663.

Loudet et al., "Colloidal ordering from phase separation in a liquid-crystalline continuous phase" *Nature*, Oct. 2000; 407(6804):611-613.

Loudet et al., "Edge dislocations of colloidal chains suspended in a nematic liquid crystal" *Europhys. Lett.*, 2001; 54:175-181.

Loudet et al., "Application of an electric field to colloidal particles suspended in a liquid-crystal solvent" *Phys. Rev. Letter.*, Oct. 2001; 87(16):165503-1-165503-4. Epub Sep. 27, 2001.

Loudet et al., "Line defect dynamics around a colloidal particle" *Eur. Phys. J. E-Soft Matter*, Mar. 2002; 7(3):205-208.

Lubensky et al., "Topological defects and interactions in nematic emulsions *Phys. Rev. E*, 1998; 57(1):610-625.

Mitov et al., "Fingerprint patterning of solid nanoparticles embedded in a cholesteric liquid crystal" *J. Phys.: Condens. Matter*; 2004; 16:S1981-S1988.

Mondain-Monval et al., "Weak surface energy in nematic dispersions: Saturn ring defects and quadrupolar interactions" *Eur. Phys. J B*, Nov. 1999 II; 12:167-170.

Poulin et al., "Novel colloidal interactions in anisotropic fluids" *Science*, Mar. 1997; 275(5307):1770-1773.

Poulin et al., "Direct measurement of colloidal forces in an anisotropic solvent" *Phys. Rev. Lett.*, Dec. 1997; 79(24):4862-4865.

Poulin et al., "Inverted and multiple nematic emulsions" *Phys. Rev. E*, 1998; 57(1):626-637.

Poulin et al., "Suspension of spherical particles in nematic solutions of disks and rods" *Phys. Rev. E*, 1999; 59(4):4384-4387.

Qi et al., "Controlled assembly of gold and silver nanoparticles using thermotropic amphiphilic and convention liquid crystals" *Proceedings of 2005 5th IEEE Conference on Nanotechnology*, Nagoya, Japan, Jul. 2005, 4 pgs.

Qi et al., "Formation of periodic strip patterns in nematic liquid crystals doped with functionalized gold nanoparticles" *J. Mater. Chem.*, 2006; 16:4197-4205.

Román-Velázquez et al., "Circular dichroism simulated spectra of chiral gold nanoclusters: A dipole approximation" *J. Phys. Chem. B*, Nov. 2003; 107(44):12035-12038.

Ruhwandl et al., "Monte Carlo simulation of topological defects in the nematic liquid crystal matrix around a spherical colloid particle" *Phys. Rev. E*, 1997; 56(5):5561-5565.

Sarathy et al., "Thiol-derivatized nanocrystalline arrays of gold, silver, and platinum" *J. Phys. Chem. B*, 1997; 101(48):9876-9880.

Schaaff et al., "Giant gold-glutathione cluster compounds: Intense optical activity in metal-based transitions" *J. Phys. Chem. B*, 2000; 104(12):2630-2641. Epub Feb. 24, 2000.

Stark et al., "Water droplets in a spherically confined nematic solvent: A numerical investigation" *Eur. Phys. J. B*, Aug. 1999 I; 10(3):515-523.

Stark, "Director field configurations around a spherical particle in a nematic liquid crystal" *Eur. Phys. J B*, Jul. 1999 II; 10(2):311-321.

Stark, "Saturn-ring defects around microspheres suspended in nematic liquid crystals: An analogy between confined geometries and magnetic fields" *Phys. Rev. E*, 2002; 66(3):032701-1-032701-2.

Svetec et al., "Annihilation of nematic point defects: Pre-collision and post-collision evolution" *Eur. Phys. J. E-Soft Matter*, May 2006; 20(1):71-79.

Tamura et al., "Chiral bisphosphine BINAP-stabilized gold and palladium nanoparticles with small size and their palladium nanoparticle-catalyzed asymmetric reaction" *J. Am. Chem. Soc.*, 2003; 125(51):15742-15743.

Templeton et al., "Monolayer-protected cluster molecules" *Acc. Chem. Res.*, 2000; 33(1):27-36.

Yao et al., "Large optical activity of gold nanocluster enantiomers induced by a pair of optically active penicillamines" *J. Am. Chem. Soc.*, 2005; 127(44):15536-15543. Epub Oct. 13, 2005.

International Search Report and Written Opinion from PCT application No. PCT/CA2007/000046; 10 pgs.

International Search Report and Written Opinion from PCT application No. PCT/CA2008/000826; 10 pgs. Dated Aug. 18, 2008.

Ahonen et al., "Formation of stable Ag-nanoparticle aggregates induced dithiol cross-linking," *J Phys Chem. B*, 2006;110:12954-12958.

Gaponik et al., "Efficient phase transfer of luminescent thiol-capped nanocrystals: from water to non-polar organic solvents," *Nano. Lett.*, 2002;2(8):803-806.

Albrecht et al., "Intrinsic multistate switching of gold clusters through electrochemical gating," *J. Am. Chem. Soc.*, 2007, 129, 9162-9167. Published online Jun. 6, 2007.

Asta et al., "Inorganic Nanoparticles—Unique Properties and Novel Applications," *Material Matters*, 2007, 2(1), 3-6.

Boettcher et al., "Tunable electronic interfaces between bulk semiconductors and ligand-stabilized nanoparticle assemblies," *Nat. Mater.*, Aug. 2007, 6, 592-596. Published online Jun. 24, 2007.

Buchnev et al., "New non-synthetic method to modify properties of liquid crystals using micro- and nano-particles," *J. Soc. Inf. Disp.*, 2005, 13(9), 749-754.

Buchnev et al., "Enhanced two-beam coupling in colloids of ferroelectric nanoparticles in liquid crystals," *J. Opt. Soc. Amer. B*, Jul. 2007, 24(7), 1512-1516. Published online Jun. 15, 2007.

Chen et al., "Electro-Optical Characteristics of a Twisted Nematic Liquid-Crystal Cell Doped with Carbon Nanotubes in a DC Electric Field," *Opt. Rev.*, 2005, 12(3), 223-225.

Ćopić et al., "Coupled director and polarization fluctuations in suspensions of ferroelectric nanoparticles in nematic liquid crystals," *Phys. Rev. E*, 2007, 76, 011702(1-5). Published online Jul. 11, 2007.

Da Cruz et al., "Phase behavior of nanoparticles in a thermotropic liquid crystal," *J Phys. Chem. B*, 2005, 109(30), 14292-14299. Published online Jul. 12, 2005.

Dark et al., "Rotational viscosity and molecular structure of nematic liquid crystals," *Liq. Cryst.*, Jan. 2006, 33(1), 67-73.

Dasog et al., "Understanding the oxidative stability of gold monolayer-protected clusters In the presence of halide ions under ambient conditions," *Langmuir*, 2007, 23, 3381-3387. Published online Feb. 2, 2007.

de la Venta et al., "Magnetism in polymers with embedded gold nanoparticles," *Adv. Mater.*, 2007, 19, 875-877. Published Feb. 19, 2007.

Dierking et al., "Aligning and Reorienting Carbon Nanotubes with Nematic Liquid Crystals," *Adv. Mater.*, Jun. 4, 2004, 16(11), 865-869. Available online Apr. 30, 2004.

Dierking, "Liquid crystal-carbon nanotubes dispersions," *J Appl. Phys.*, 2005, 97, 044309(1-5). Published online Jan. 25, 2005.

Dierking et al., "Magnetically steered liquid crystal-nanotube switch," *Appl. Phys. Lett.*, 2005, 87, 233507(1-3).

Diorio Jr. et al., "The electro-optic properties of colloidal silica filled nematics," *Liq. Cryst.*, 2002, 29(4), 589-596.

Drawhorn et al., "Anchoring of nematic liquid crystals on self-assembled monolayers formed from alkanethiols on semitransparent films of gold," *J. Phys. Chem.*, 1995, 99, 16511-16515. Abstract published in *Advance ACS Abstracts* Nov. 1, 1995.

Dunmur et al., "Elastic Properties," in *Handbook of Liquid Crystals*, Demus et al. (Eds.), Wiley-VCH (Weinheim), 1998, vol. 1, pp. 253-280.

Eidenschink et al., "Static scattering in filled nematic: new liquid crystal display technique," *Electron. Lett.*, Jun. 20, 1991, 27(13), 1195-1196.

Elston et al., The Optics of Thermotropic Liquid Crystals, Taylor & Francis, Bristol, PA, 1998, cover page, copyright page, and table of contents only; 4 pgs.

Freedericksz et al., "Über die Orientierung anisotropen Flüssigkeiten in dünnen Schichten und die Messung einiger Ihre elastischen eigenshaften charakterisierenden Konstanten," *Phys. Z. Sow.*, 1934, 6, 490-504.

Frisken et al., "Freedericksz transitions in nematic liquid crystals: The effects of an in-plane electric field," *Phys. Rev. A*, Nov. 15, 1989, 40(10), 6099-6102.

Glushchenko et al., "Memory effect in filled nematic liquid crystals," *Liq. Cryst.*, 1997, 23(2), 241-246.

Guzmán et al., "Quenched disorder in a liquid-crystal biosensor: Adsorbed nanoparticles at confining walls," *J. Chem. Phys.*, May 8, 2005, 122, 184711(1-10). Published online May 11, 2005.

Haraguchi et al., "Reduction of the threshold voltages of nematic liquid crystal electrooptical devices by doping inorganic nanoparticles," *Jpn. J. Appl. Phys.*, 2007, 46(34), 796-797.

Hegmann et al., "Nanoparticles in Liquid Crystals: Synthesis, Self-Assembly, Defect Formation and Potential Applications," *J. Inorg. Organomet. Polym. Mater.*, Sep. 2007, 17(3), 483-508.

Hegmann et al., "Alignment and Electro-Optic Effects of Funcationalized Gold Nanoparticles and CdTe Semiconductor Quantum Dots in Nematic Hosts" abstract, Canadian Society for Chemistry (CSC), Ottawa, Ontario, Canada, 2009, retrieved on May 14, 2009 from the internet <http://abstracts.csc2009.ca/00000289.htm>; 1 pg.

Hong et al., "Extraordinarily high-contrast and wide-view liquid crystal displays," *Appl. Phys. Lett.*, 2005, 86, 121107(1-3). Published online Mar. 15, 2005.

Huang et al., "Electrooptical Responses of Carbon Nanotube-Doped Liquid Crystal Devices," *Jpn. J. Appl. Phys.*, Nov. 9, 2005, 44(11), 8077-8081.

Huang et al., "Electrooptical Properties of Carbon-Nanotube-Doped Twisted Nematic Liquid Crystal Cell," *Jpn. J. Appl. Phys.*, Aug. 4, 2006, 45(8A), 6392-6394.

Jeon et al., *Appl. Phys. Lett.*, "Effects of carbon nanotubes on electro-optical characteristics of liquid crystal cell driven by in-plane field," Mar. 2007, 90(12), 121901(1-3).

Jeong et al., "Electroactive Superelongation of Carbon Nanotube Aggregates in Liquid Crystal Medium," *Nano Lett.*, 2007, 7(8), 2178-2182. Available online Jul. 4, 2007.

Kaur et al., "Enhanced electro-optical properties in gold nanoparticles doped ferroelectric liquid crystals," *Appl. Phys. Lett.*, 2007, 91, 023120(1-3). Published online Jul. 13, 2007.

Khoo, *Liquid Crystals*, $2^{nd}$ ed.; John Wiley & Sons, Hoboken, NJ, 2007, cover page, copyright page, and table of contents; 9 pgs. Available online May 18, 2006.

Kinkead et al., "Effects of size, capping agent, and concentration of CdSe and CdTe quantum dots doped into a nematic liquid crystal on the optical and electro-optic properties of the final colloidal liquid crystal mixture," *J. Mater. Chem.*, 2010, 20(3): 448-458. Available online Nov. 6, 2009 as an Advance Article.

Knobloch et al., "Command surface controlled liquid crystal waveguide structures as optical information storage," *J. Appl. Phys.*, Dec. 15, 1994, 76(12), 8212-8214.

Knobloch et al., "Photochromic command surface induced switching of liquid crystal optical waveguide structures," *J. Appl. Phys.*, Jan. 15, 1995, 77(2), 481-487.

Kobayashi et al., "Dielectric spectroscopy of metal nanoparticle doped liquid crystal displays exhibiting frequency modulation response," *J. Display Technol.*, Jun. 2006, 2(2), 121-129.

Kossyrev et al., "Electric field tuning of plasmonic response of nanodot array in liquid crystal matrix," *Nano Lett.*, 2005, 5(10), 1978-1981. Published online Sep. 9, 2005.

Kreuzer et al., "Erasable optical storage in bistable liquid-crystal cells," *Mol. Cryst. Liq. Cryst.*, 1992, 223, 219-227. First published Jan. 1, 1992.

Lapointe et al., "Elastic torque and the levitation of metal wires by a nematic liquid crystal," *Science*, Jan. 30, 2004, 303, 652-655.

Lee et al., "Effects of carbon-nanotube doping on the performance of a TN-LCD," *J. Soc. Inf. Disp.*, Sep. 2005, 13(9), 743-747.

Li et al., "Shape and Aggregation Control of Nanoparticles: Not Shaken, Not Stirred," *J. Am. Chem. Soc.*, 2006, 128(3), 968-975. Available online Dec. 31, 2005.

Li et al., "Ferroelectric nanoparticle/liquid-crystal colloids for display applications," *J. Soc. Inf. Disp.*, 2006, 14(6), 523-527.

Li et al., "Orientational coupling amplification in ferroelectric nematic colloids," *Phys. Rev. Lett.*, Oct. 6, 2006, 97(14), 147801(1-4). Published online Oct. 5, 2006.

Maye et al., "Heating-induced evolution of thiolate-encapsulated gold nanoparticles: a strategy for size and shape manipulations," *Langmuir*, 2000, 16(2), 490-497. Published online Nov. 4, 1999.

Mitov et al., "Long-range structuring of nanoparticles by mimicry of a cholesteric liquid crystal," *Nat. Mater.*, Dec. 2002, 1, 229-231. Published online Nov. 17, 2002.

Miyama et al., "Fast switching of frequency modulation twisted nematic liquid crystal display fabricated by doping nanoparticles and its mechanism," *Jpn. J. Appl. Phys.*, 2004, 43(5A), 2580-2584.

Miyama et al., "Dielectric properties and electro-optic characteristics of TN-LCDs doped with metal nanoparticles exhibiting frequency modulation response accompanying fast response," *Mol. Cryst. Liq. Cryst.*, 2005, 433(1), 29-40. Published online Jun. 1, 2005.

Ouskova et al., "Dielectric relaxation spectroscopy of a nematic liquid crystal doped with ferroelectric $Sn_2P_2S_6$ nanoparticles," *Liq. Cryst.*, Oct. 2003, 30(10), 1235-1239.

Peceros et al., "Dipole-dipole plasmon interactions in gold-on-polystyrene composites," *J. Phys. Chem. B*, 2005, 109(46), 21516-21520. Published online Sep. 9, 2005.

Pietron et al., "Using electrons stored on quantized capacitors in electron transfer reactions," *J. Am. Chem. Soc.*, 1999, 121(23), 5565-5570. Published online May 26, 1999.

Prasad et al., "Electrical conductivity and dielectric constant measurements of liquid crystal-gold nanoparticle composites," *Liq. Cryst.*, Oct. 2006, 33(10), 1121-1125.

Qi et al., "Effects of hydrophilic and hydrophobic gold nanoclusters on the stability and ordering of bolaamphiphilic liquid crystals," *J. Mater. Chem.*, 2007; 17:2139-2144. First published as an Advance Article on the web Mar. 8, 2007.

Qi et al., "Chirality transfer in nematic liquid crystals doped with (S)-naproxen functionalized gold nanoclusters: an induced circular dichroism study," *J. Mater. Chem.*, 2008; 18: 374-380. First published as an Advance Article on the web Dec. 4, 2007.

Qi et al., "Unprecedented Dual Alignment Mode and Freedericksz Transition in Planar Nematic Liquid Crystal Cells Doped with Gold Nanoclusters," *Adv. Funct. Mater.*, Jan. 24, 2008, 18(2), 212-221. Available online Jan. 3, 2008.

Qi et al., "Impact of nanoscale particles and carbon nanotubes on current and future generations of liquid crystal displays," *J. Mater. Chem.*, 2008, 18(28), 3288-3294.

Qi et al., "Effects of functionalized metal and semiconductor nanoparticles in nematic liquid crystal phases," *Proc. SPIE-Int. Soc. Opt. Eng.*, 2008, 6911, 691106(1-11).

Qi et al., "Miscibility and Alignment Effects of Mixed Monolayer Cyanobiphenyl Liquid-Crystal-Capped Gold Nanoparticles in Nematic Cyanobiphenyl Liquid Crystal Hosts," *ChemPhysChem.*, Jun. 2, 2009, 10(8), 1211-1218. Available online Mar. 30, 2009.

Reshetnyak, "Effective dielectric function of ferroelectric LC suspensions," *Mol. Cryst. Liq. Cryst.*, 2004, 421(1), 219-224. Published online Jan. 1, 2004.

Reshetnyak et al., "Freedericksz transition threshold in nematic liquid crystals filled with ferroelectric nano-particles," *Mol. Cryst. Liq. Cryst.*, 2006, 454, 201/[603]-206/[608].

Reznikov et al., "Ferroelectric nematic suspension," *Appl. Phys. Lett.*, Mar. 24, 2003, 82(12), 1917-1919.

Sage, "Displays" in *Handbook of Liquid Crystals*, Wiley-VCH, Weinheim, Demus et al. (Eds.), vol. 1, 1998, pp. 731-762.

Sano et al., "Enhancement of characteristics of LCDs by doping nanoparticles: reduction of operating voltage, viscosity, and response times," *Proc. SPIE*, 2006, 613501(1-5).

Schadt, "Liquid crystal materials and liquid crystal displays," *Ann. Rev. Mater. Sci.*, 1997, 27, 305-379.

Shipway et al., "Nanoparticle arrays on surfaces for electronic, optical, and sensor applications," *ChemPhysChem*, 2000, 1, 18-52.

Sikharulidze, "Nanoparticles: An approach to controlling an electro-optical behaviour of nematic liquid crystals," *Appl. Phys. Lett.*, 2005, 86, 033507(1-3). Published online Jan. 14, 2005.

Song et al., "Nematic Liquid Crystallinity of Multiwall Carbon Nanotubes," *Science*, Nov. 21, 2003, 302(5649), 1363.

Sonin, *The surface physics of liquid crystals*, 1995, Gordon & Breach, Luxembourg; cover page, copyright page, and table of contents only; 5 pgs.

Stark, "Physics of colloidal dispersions in nematic liquid crystals," *Phys. Rep.*, 2001, 351, 387-474.

Stark, "Geometric view on colloidal interactions above the nematic-isotropic phase transition," *Phys. Rev. E*, Oct. 30, 2002, 66, 041705(1-4).

Tatumi et al., "Recent liquid crystal material development for active matrix displays," *Ann. Rev. Mater. Sci.*, 1997, 27, 423-441.

Terrill et al., "Monolayers in three dimensions: NMR, SAXS, thermal, and electron hopping studies of alkanethiol stabilized gold clusters," *J Am. Chem. Soc.*, 1995, 117(50), 12537-12548.

Toney et al., "Near-surface alignment of polymers in rubbed films," *Nature*, Apr. 20, 1995, 374, 709-711.

Wang et al., "Correlations between liquid crystal director reorientation and optical response time of a homeotropic cell," J. Appl. Phys., May 15, 2004, 95(10), 5502-5508.

West et al., "Colloidal particles at a nematic-isotropic interface: Effects of confinement," *Eur. Phys. J. E*, 2006, 20, 237-242. Published online Jun. 22, 2006.

Williams et al., "Electro-optical and nonlinear optical properties of semiconductor nanorod doped liquid crystals," *Proc. SPIE*, 2005, 5936, 593613(1-6).

Wu et al., "Physical-properties of chlorinated liquid crystals," *Liq. Cryst.*, Nov. 1991, 10(5), 635-646.

Wuelfing et al., "Electronic conductivity of solid-state, mixed-valent, monolayer-protected Au clusters," *J. Am. Chem. Soc.*, 2000, 122(46), 11465-11472. Published online Nov. 5, 2000.

Yakuphanoglu et al., "Conductance and dielectric anisotropy properties of 4-cyano-4'-hexylbiphenyl-salicylaldimine compound composite liquid crystal exhibiting large positive dielectric anisotropy" *Physica B: Physics of Condensed Matter*, Apr. 30, 2007, 393(1-2), 270-274.

Yamamoto et al., "Direct observation of the ferromagnetic spin polarization in gold nanoparticles: A review," *Rev. Adv. Mater. Sci.*, 2006, 12, 23-32.

Yoshikawa et al., "Frequency modulation response of a tunable birefringent mode nematic liquid crystal electrooptic device fabricated by doping nanoparticles of Pd covered with liquid-crystal molecules," *Jpn. J. Appl. Phys.*, 2002, 41 (Part 2, No. 11B), 1315-1317.

Zapotacky et al., "Particle-stabilized defect gel in cholesteric liquid crystals," *Science*, Jan. 8, 1999, 283, 209-212.

Periodic Stripe Texture (local chiral domains)

Nematic Texture (non-chiral)

METAL NANOPARTICLE AND USE THEREOF FOR INDUCING CHIRALITY IN LIQUID CRYSTAL PHASES

This application is the §371 U.S. National Stage of International Application No. PCT/CA2007/000046, filed 12 Jan. 2007, which claims the benefit of U.S. Provisional Application Ser. No. 60/758,201, filed 12 Jan. 2006, all of which are incorporated herein by reference in their entirety.

FIELD OF THE INVENTION

The present invention relates to a metal nanoparticle and use thereof for inducing chirality in liquid crystal phases.

BACKGROUND OF THE INVENTION

Nematic liquid crystals (LCs) are one-dimensionally ordered fluids commonly formed by rod-shaped molecules. Dispersed colloidal particles disrupt the nematic order, and minimization of the elastic energy leads to the formation of anisotropic colloidal structures.[1] Sufficiently large particles, depending on the strength and direction of the nematic anchoring on the particle surface, can form various types of topological defects such as Saturn rings, hyperbolic hedgehogs, and boojums in agreement with theoretical considerations.[2-7] Past experimental studies focused on dispersions of water microdroplets,[1,8,9] ferro-fluids,[10] gold coated glass spheres,[11] or silicon oil[12-15] in nematic LCs (N-LCs) as well as latex particles in lyotropic LCs.[9,16] For most particles, if the nematic LC molecules are strongly and perpendicularly anchored at the surface of a spherical particle, the particles act like a radial hedgehog carrying a topological charge. Placed in a uniformly aligned nematic solvent to satisfy the boundary conditions at infinity, the particle should nucleate a further defect in its nematic environment. As theoretically predicted,[17,18] the dipole is the preferred configuration for large particles and sufficiently strong anchoring, although quadrupoles are also observed.[11] The topological dipole formed by one quasi-spherical particle and an accompanying topological defect, known as a hyperbolic hedgehog, generate elastic forces that lead to the formation of chain-like particle aggregates.[19] However, the interactions between colloidal particles and the nematic LC molecules strongly depend on the particular combination of the two materials, the molecular structure and elastic properties of the LC, as well as on the type and likely the size and shape of the colloidal particle used.

Recent theoretical studies on the structural properties of gold nanoclusters have shown that the most stable (lowest energy) isomers of bare $Au_{28}$, $Au_{55}$ as well as thiol-protected clusters (e.g., $Au_{28}(SCH_3)_{16}$) correspond to chiral nanostructures.[20] These findings provide support for the existence of chirality in noble metal clusters suggested by the intense optical activity measured in the metal-based electronic transitions of size-separated glutathione-protected gold particles in the size range of 20 to 40 atoms.[21] Further theoretical work, based on quantifying chirality via the Hausdorff chirality measure (HCM),[20,22,23] predicts that strong structural distortions in a gold cluster upon thiol protection could, for example, induce chirality in an achiral unprotected cluster.[20]

In addition to the work of Whetten et al. on glutathione capped gold nanoparticles,[21] the groups of Fujihara and Yao reported, for example, on the syntheses of optically active nanoclusters protected with chiral (R)- and (S)-BINAP[24] or penicillamines[25] (D-Pen, L-Pen, and racemate). It is important to note that all three groups used enantiomeric species of the capping agent for the synthesis of their gold nanoparticles resulting in enantiopure particles with an optical activity that is easily identified by circular dichroism (CD) spectroscopy. However, it appears that none of the considerably complex CD spectra in the UV regions, the CD signals at wavelengths where the used protecting agent does not absorb as well as an inversion of the ellipticity, and θ (mirror image) from free capping agent to the capped nanocluster[25] can not be explained by the chirality of the capping agent itself. Hence, the structured CD spectra are likely due to the quantized electronic transitions and their interactions in the cluster, which indicates, as theory predicts,[20] that nanoparticles can indeed form well-defined stereostructures as 'normal' chiral molecules do.

Circular Dichroism is observed when optically active matter absorbs left and right handed circularly polarized light with a different absorption coefficient. Another sensitive probe for molecular chirality are liquid crystalline phases, in particular the nematic phase. Nematic liquid crystals are one-dimensionally ordered fluids commonly formed by rod-shaped molecules. It has been known for a long time that doping nematic phases with chiral, nonracemic compounds (chiral additives or dopants) transforms them into chiral nematic phases,[26] characterized by a helical spatial arrangement of the director. In this chiral structure, the anisotropic molecules rotate in a helical manner to form lamellae of equally spaced planes with a common molecular orientation. Polarizing optical microscopy (POM) commonly provides direct evidence of the chirality induced by a chiral dopant in a non-chiral nematic liquid crystal. Characteristic textures and defect structures clearly reveal the difference between chiral and non-chiral nematic phases. Depending on the boundary conditions (planar, homeotropic), between crossed polarizers nematic liquid crystals such as Felix-2900-03 usually produce so-called Schlieren (FIG. 1), marble or thread-like textures, whereas the chiral nematic phase induced by doping 5 wt % of a chiral dopant such as (S)-Naproxen into Felix-2900-03 can display so-called oily-streak, fan-like, fingerprint (FIG. 2) or cholesteric finger textures.[27]

SUMMARY OF THE INVENTION

According to one aspect of the present invention, there is provided a metal nanoparticle comprising: a metal; and a chiral group bonded to the metal.

According to another aspect of the present invention, there is provided a colloidal suspension or dispersion comprising: a metal nanoparticle comprising a metal and a chiral group bonded to the metal; and a liquid crystal.

According to still another aspect of the present invention, there is provided a process for preparing a metal nanoparticle as described herein comprising: providing a solution comprising $HAuCl_4$ and a thiol comprising a chiral group; and reducing $HAuCl_4$ with a reducing agent.

According to yet another aspect of the present invention, there is provided a use of a metal nanoparticle comprising: a metal and a thiolate group bonded to the metal; as a chiral dopant in a liquid crystal.

According to a further aspect of the present invention, there is provided a colloidal suspension or dispersion comprising: a metal nanoparticle comprising a metal and a thiolate group bonded to the metal; and a liquid crystal.

According to still a further aspect of the present invention, there is provided a method for determining chirality or local chiral effects of a metal nanoparticle comprising: mixing a non-chiral nematic liquid crystal with a metal nanoparticle; and identifying a textural change in the non-chiral nematic liquid crystal to a nematic liquid crystal thin film showing birefringent stripe domains (colored when viewed with crossed polarizers as well as parallel polarizers), wherein the presence of the textural change indicates a sort of chirality transfer or local induction of chiral interfaces by the metal nanoparticle.

According to another aspect of the present invention, there is provided a method for transferring chirality to a liquid crystal comprising: providing a liquid crystal; and doping the liquid crystal with a metal nanoparticle comprising a metal and a chiral group bonded to the metal.

According to still another aspect of the present invention, there is provided a method for transferring chirality to a liquid crystal comprising: providing a liquid crystal; and doping the liquid crystal with a gold nanoparticle comprising gold and a thiolate group bonded to the gold.

BRIEF DESCRIPTION OF THE DRAWINGS

In the accompanying drawings, which illustrate an exemplary embodiment of the present invention.

DETAILED DESCRIPTION OF THE INVENTION

Metal Nanoparticles

Figure 1:
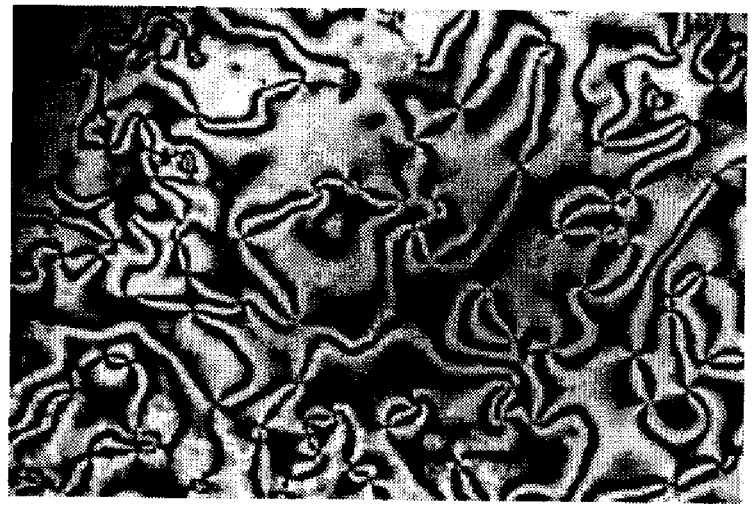
FIG. 1 is a polarizing optical microscopy (POM) micrograph (crossed polarizers) of the high temperature liquid crystal phase taken at 68° C. upon cooling from the isotropic-nematic phase transition showing the nematic Schlieren texture of Felix-2900-03.
Figure 2:
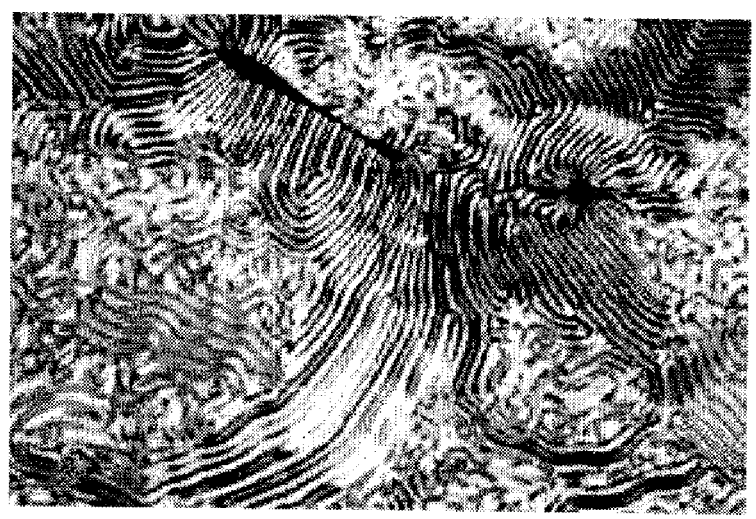
FIG. 2 is a POM micrograph (crossed polarizers) of the high temperature liquid crystal phase taken at 44° C. upon cooling from the isotropic-nematic phase transition showing the fingerprint texture of N* phase of Felix-2900-03 doped with 5 wt % Naproxen.

The present invention relates to a metal nanoparticle comprising a metal and chiral group bonded to the metal.

The metal of the metal nanoparticle may be, for example, gold, silver, platinum, or palladium. In a preferred embodiment, the metal is gold. Chirality is imparted to the metal nanoparticles by a chiral group bonded to the metal.

The chiral group may be bonded to the metal through any one of a variety of linkages, for example, a thiol linkage, a bis-thiol linkage, a thiosulfate linkage, or phosphorous linkage. In a preferred embodiment, the linkage is a thiol linkage, such as alkylthiol.

Generally, alkylthiols provide a stable monolayer protection for functionalized gold nanoparticles. The nanoparticles were synthesized using a modified Brust-Schiffrin procedure[28]. For example, Au1 was synthesized using a Brust-Schiffrin two phase method with a phase transfer agent such as tetraoctylammonium bromide (TOAB). The one phase method does not require the use of phase transfer agents, and provides gold nanoparticles that are stable under ambient conditions and to elevated temperature up to at least 120° C.

Thiol-protected silver[29] and platinum[30] nanoparticles may be prepared in the same size regime as the gold nanoparticles. Since the local chiral effect produced by the straight alkylthiol protected gold nanoparticles leading to the formation of birefringence of the stripes is only a result of a local twist of the director (coinciding with the long molecular axis of the nematic LC), silver and platinum nanoparticles, in the same size regime, should produce the same effects if dispersed in a non-chiral nematic liquid crystal. In the same sense, chirally-modified silver and platinum nanoparticles (bearing chiral dopant structures) should also produce chiral phenomena in non-chiral nematic liquid crystals.

The linkage may also comprise a spacer group, for example, an aliphatic group such as $C_{4-18}$ alkyl. The length of the spacer group depends on whether it is functionalized with a chiral or liquid crystal (pro-mesogenic) moiety since thiol functionalized metal nanoparticles undergo aggregation and so-called Ostwald ripening (aggregation and sintering to form a larger particle)[31] at elevated temperatures depending on the length of the aliphatic chain. Therefore, metal nanoparticles with 'simple' straight alkylthiols may be used with a spacer group having a length in the range of $C_{6-18}$, and metal nanoparticles protected with alkylthiols that are functionalized with pro-mesogenic, liquid crystal and/or chiral moieties may be used with a spacer group having a length in the range of $C_{4-18}$.

Spacer groups may also be linked. For example, if a bis-thiol linkage such as thioctic acid is employed, the alkyl spacer groups may be linked via an ester linkage.

The chiral group may be any group having one or more chiral centers. For example, the chiral group may be a chiral ester such as 6-sulfanylhexyl (2S)-(6-methoxy-2-naphthyl)propanoate, 12-sulfanyldodecyl (2S)-(6-methoxy-2-naphthyl)propanoate, (2S)-methylbutyl 7-sulfanylheptanoate, or an enantiomer thereof.

Other chiral groups, particularly those commonly used as chiral dopants for inducing chiral nematic liquid crystalline phases should also produce local and overall chiral effect in non-chiral nematic liquid crystals or liquid crystal mixtures. Given that the chiral dopants can be well-dispersed in the nematic liquid crystal host, the chiral dopant should, if reported to induce a chiral nematic phase when not linked to a metal nanoparticle, also work when linked to a metal nanoparticle in the same size regime. Such other chiral groups could contain atropisomeric cores, cholesterol structures or generally rod-like rigid segments with chiral centers in the attached side chains similar to the (S)-Naproxen functionalized thiols.

The metal nanoparticle may also be a mixed monolayer protected nanoparticle such that groups bonded to the metal are not all identical and/or not all chiral. For example, a non-chiral group may also be bonded to the metal through any one of a variety of linkages, for example, a thiol linkage, a bis-thiol linkage, a thiosulfate linkage, or phosphorous linkage. In a preferred embodiment, the non-chiral group is a $C_{4-18}$ alkyl thiolate such as hexanethiol or dodecanethiol. The mixed monolayer protected nanoparticle may, for example, comprise a chiral group formed from a chiral ester such as 6-sulfanylhexyl (2S)-(6-methoxy-2-naphthyl)propanoate, 12-sulfanyldodecyl (2S)-(6-methoxy-2-naphthyl)propanoate, (2S)-methylbutyl 7-sulfanylheptanoate, or an enantiomer thereof, and a non-chiral group such as hexanethiol or dodecanethiol. The ratio of chiral to non-chiral groups may be in the range of about 5:1 to about 1:5, about 4:1 to about 1:5, about 3:1 to about 1:5, about 2:1 to about 1:5, about 1:1 to about 1:5, about 1:2 to about 1:5, about 1:3 to about 1:5, about 1:4 to about 1:5, about 5:1 to about 1:4, about 5:1 to about 1:3, about 5:1 to about 1:2, about 5:1 to about 1:1, about 5:1 to about 2:1, about 5:1 to about 3:1, about 5:1 to about 4:1, about 4:1 to about 1:4, about 3:1 to about 1:3, about 2:1 to about 1:2, about 5:1, about 4:1, about 3:1, about 2:1, about 1:1, about 1:2, about 1:3, about 1:4 or about 1:5.

For mixed monolayer protected metal nanoparticles, the ratio depends on the ratio of the two thiols used during the modified Brust-Schiffrin procedure. For the mixed cluster Au4 described herein, a 1:1 ratio of starting thiols resulting in the formation of a metal nanoparticle protected with the two thiols in a ratio of 2:1. However, this ratio likely also depends on the type of thiols used in the synthesis as well as on the synthesis itself, i.e. if using the place exchange reaction[32] for introducing the second thiol starting with a hexane thiolate-coated metal nanoparticle.

In a preferred embodiment, the metal nanoparticle comprising a metal and a chiral group bonded to the metal as described herein may be:

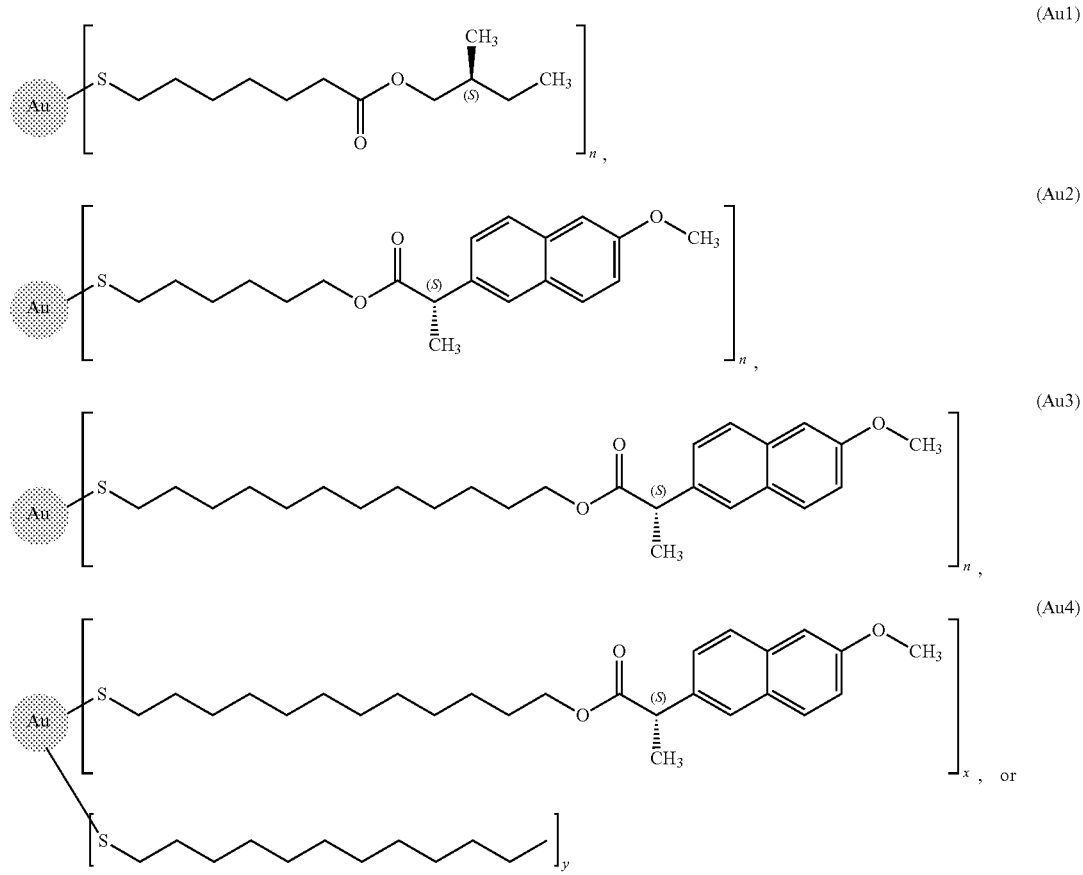

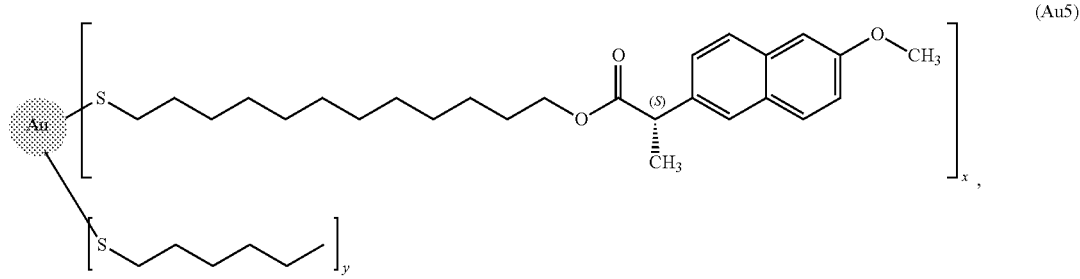

(Au5)

wherein n is greater than or equal to (1) one, and x and y are in a ratio of about 5:1 to about 1:5, more preferably about 1:1 or about 1:2.

The present invention also relates to a metal nanoparticle comprising a metal and thiolate group bonded to the metal.

The metal of the metal nanoparticle may be, for example, gold, silver, platinum, or palladium. In a preferred embodiment, the metal is gold.

The thiolate group may be chiral or non-chiral.

In the case where the thiolate group is chiral, it may comprise any group with one or more chiral centers. For example, the thiolate group may comprise a chiral ester.

In a preferred embodiment, the thiolate group may be a chiral ester such as 6-sulfanylhexyl (2S)-(6-methoxy-2-naphthyl)propanoate, 12-sulfanyldodecyl (2S)-(6-methoxy-2-naphthyl)propanoate, (2S)-methylbutyl 7-sulfanylheptanoate, or an enantiomer thereof.

In the case where the thiolate group is non-chiral, it may be a $C_{4-18}$ alkyl thiolate optionally substituted with one or more substituents. Such substituents may include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety.

In a preferred embodiment, the thiolate group may be, for example, hexanethiol or dodecanethiol.

The metal nanoparticle comprising a metal and a thiolate group bonded to the metal as described herein may also be a mixed monolayer protected nanoparticle such that thiolate groups bonded to the metal are not all identical, more specifically the chemical nature and the chirality of the thiolate groups need not be identical.

In a preferred embodiment, the mixed monolayer protected nanoparticle may, for example, comprise a thiolate group formed from a combination of thiols such as 6-sulfanylhexyl (2S)-(6-methoxy-2-naphthyl)propanoate, 12-sulfanyldodecyl (2S)-(6-methoxy-2-naphthyl)propanoate, (2S)-methylbutyl 7-sulfanylheptanoate, hexanethiol or dodecanethiol.

In a preferred embodiment, the metal nanoparticle comprising a metal and a thiolate group bonded to the metal may be:

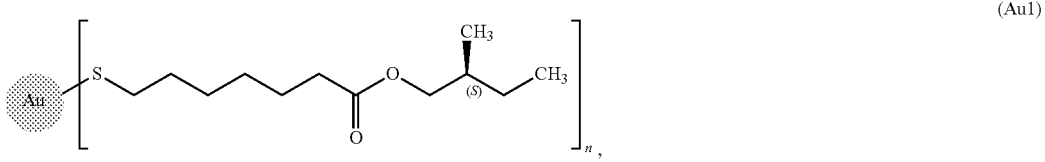

(Au1)

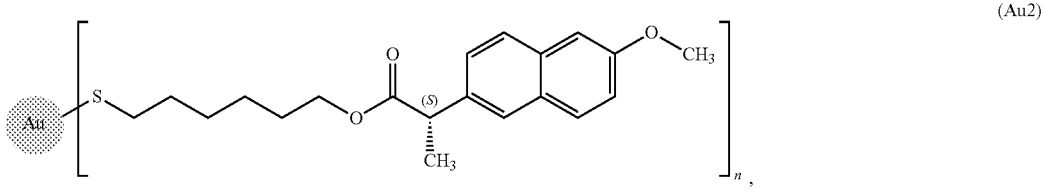

(Au2)

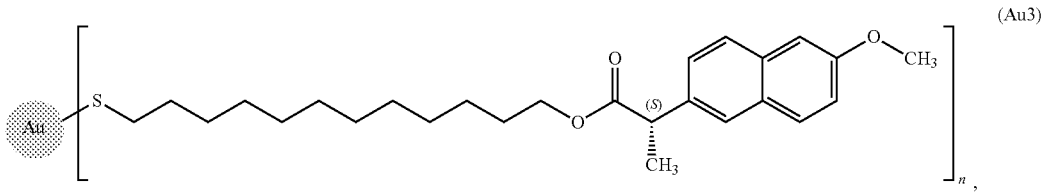

(Au3)

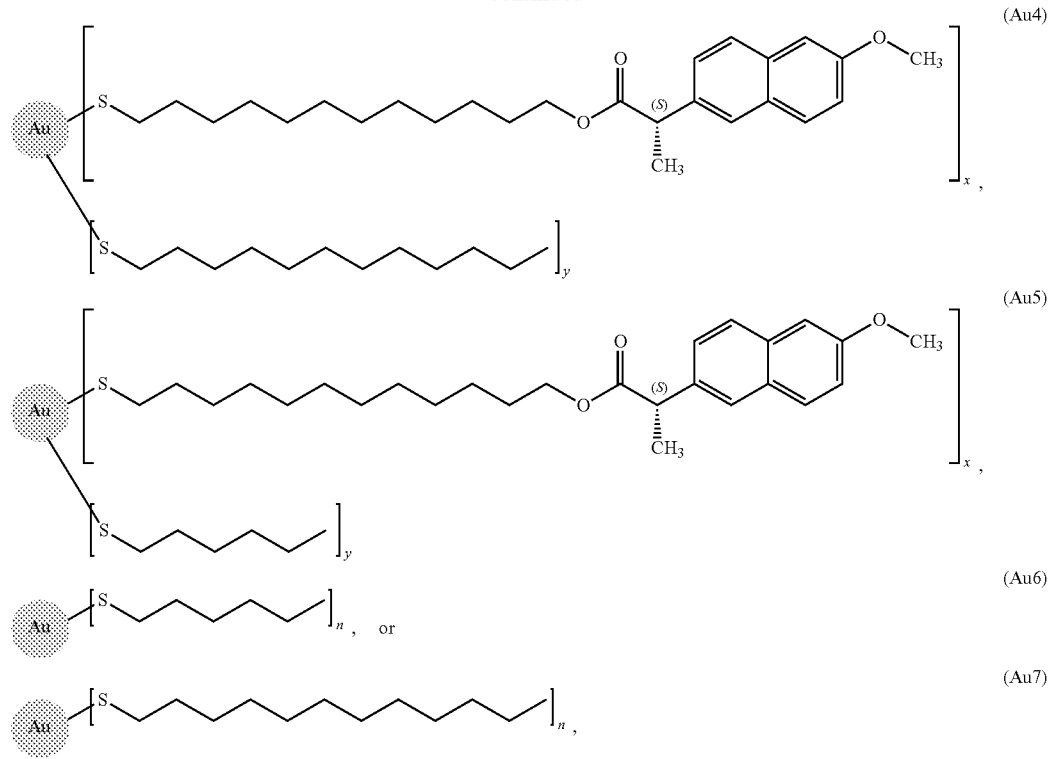

wherein n is greater than or equal to (1) one, and x and y are in a ratio of about 5:1 to about 1:5, more preferably about 1:1 or about 1:2.

The metal nanoparticles described herein may further comprise a luminescent atom or group. Examples of such atoms or groups are lanthanide atoms doped into the metal core or organic dyes on the surface of the metal via the spacer groups.

Luminescent functionalities may be introduced and should not interfere with the domain formation and the chirality transfer. The reason for introducing luminescent groups is twofold: (i) application and self-illumination for device applications, and (ii) to study the assembly process by techniques such as fluorescence microscopy. Two possible ways to introduce luminescence (electro- or photo-luminescence) into these materials are: (i) using fluorescently labeled thiols during the particle synthesis using common fluorescent dyes (with rod-like shape), and (ii) using doped metal nanoparticles (some of which are commercially available). In principle, both ways of introducing luminescence will neither interfere with the assembly process nor with the chiral effects due to chirality transfer or to local twist of the director configuration.

The average size of the metal nanoparticles described herein may be, for example, from about 1 nm to about 100 nm, from about 1 nm to about 90 nm, from about 1 nm to about 80 nm, from about 1 nm to about 70 nm, from about 1 nm to about 60 nm, from about 1 nm to about 50 nm, from about 1 nm to about 40 nm, from about 1 nm to about 30 nm, from about 1 nm to about 20 nm, from about 1 nm to about 10 nm, from about 10 nm to about 100 nm, from about 20 nm to about 100 nm, from about 30 nm to about 100 nm, from about 40 nm to about 100 nm, from about 50 nm to about 100 nm, from about 60 nm to about 100 nm, from about 70 nm to about 100 nm, from about 80 nm to about 100 nm, from about 90 nm to about 100 nm, from about 20 nm to about 90 nm, from about 30 nm to about 80 nm, from about 40 nm to about 70 nm, from about 50 nm to about 60 nm, from about 1 nm to about 10 nm, from about 1 nm to about 9 nm, from about 1 nm to about 8 nm, from about 1 nm to about 7 nm, from about 1 nm to about 6 nm, from about 1 nm to about 5 nm, from about 1 nm to about 4 nm, from about 1 nm to about 3 nm, from about 1 nm to about 2 nm, from about 2 nm to about 10 nm, from about 3 nm to about 10 nm, from about 4 nm to about 10 nm, from about 5 nm to about 10 nm, from about 6 nm to about 10 nm, from about 7 nm to about 10 nm, from about 8 nm to about 10 nm, from about 9 nm to about 10 nm, from about 2 nm to about 9 nm, from about 3 nm to about 8 nm, from about 4 nm to about 7 nm, from about 5 nm to about 6 nm, from about 2 nm to about 5 nm, about 1 nm, about 2 nm, about 3 nm, about 4 nm, about 5 nm, about 6 nm, about 7 nm, about 8 nm, about 9 nm, about 10 nm, about 20 nm, about 30 nm, about 40 nm, about 50 nm, about 60 nm, about 70 nm, about 80 nm, about 90 nm, or about 100 nm.

Process for Preparing a Metal Nanoparticle

The present invention also relates to a process for preparing a metal nanoparticle as described herein when the metal is gold. The process comprises providing a solution comprising $HAuCl_4$ and a compound having a chiral or non-chiral thiolate group; and reducing the $HAuCl_4$ with a reducing agent.

For example, the compound having a chiral and/or non-chiral thiolate group may be 6-sulfanylhexyl (2S)-(6-methoxy-2-naphthyl)propanoate, 12-sulfanyldodecyl (2S)-(6-methoxy-2-naphthyl)propanoate, (2S)-methylbutyl 7-sulfanylheptanoate, hexanethiol or dodecanethiol.

The reducing agent may be for example a complex hydride such as $NaBH_4$ or $LiAlH_4$.

The solvent used for the solution comprising $HAuCl_4$ and a compound having a chiral group may be tetrahydrofuran, toluene, hexane or a mixture thereof. The solution may also be biphasic requiring the use of a phase transfer agent.

Use of Metal Nanoparticles with a Liquid Crystal

The present invention also relates to a metal nanoparticle as described herein for use as a chiral dopant in a non-chiral liquid crystal phase. Examples of liquid crystal phases are nematic phases, such as uniaxial, biaxial, or discotic; smectic phases, such as smectic A, smectic C, or hexatic; and banana phases produced by bent-core liquid crystals or discotic liquid crystals. In a preferred embodiment, the liquid crystal may be Felix-2900-03

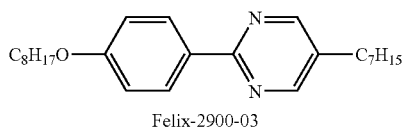

Felix-2900-03 or a cyanobiphenyl derivative such as 4'-n-pentyl-4-cyanobiphenyl (5CB), 4'-n-octyl-4-cyanobiphenyl (8CB) or 4'-n-octyloxy-4-cyanobiphenyl (8OCB), or other nematic LCs or LC mixtures.

Liquid crystal modified thiols may be used. The use of cyanobiphenyls (common nematic liquid crystals) results in a higher compatibility between metal nanoparticles and the liquid crystal host due to the liquid crystal functionalization of the metal nanoparticle surface maximizing interactions between the two components. Also a combination of chiral units such as (S)-Naproxen and alkylthiol functionalized cyanobiphenyls may be used.

Characterization of the nanoparticle doped nematic phase of Felix-2900-03 by polarized optical microscopy revealed the formation of textures similar to textures commonly formed by chiral nematic liquid crystalline phases, namely the formation of so-called cholesteric finger-like textures (striped textures) due to the formation of topological defects coupled with either induced chirality (chirally modified metal nanoparticles), or local chiral twist (non-chiral metal nanoclusters).

The present invention also relates to a colloidal suspension or dispersion comprising a metal nanoparticle as described herein and a liquid crystal.

The colloidal suspension or dispersion described herein may comprise, for example, from about 1 to about 20%, from about 2 to about 20%, from about 3 to about 20%, from about 4 to about 20%, from about 5 to about 20%, from about 6 to about 20%, from about 7 to about 20%, from about 8 to about 20%, from about 9 to about 20%, from about 10 to about 20%, from about 11 to about 20%, from about 12 to about 20%, from about 13 to about 20%, from about 14 to about 20%, from about 15 to about 20%, from about 16 to about 20%, from about 17 to about 20%, from about 18 to about 20%, from about 19 to about 20%, from about 1 to about 19%, from about 1 to about 18%, from about 1 to about 17%, from about 1 to about 16%, from about 1 to about 15%, from about 1 to about 14%, from about 1 to about 13%, from about 1 to about 12%, from about 1 to about 11%, from about 1 to about 10%, from about 1 to about 9%, from about 1 to about 8%, from about 1 to about 7%, from about 1 to about 6%, from about 1 to about 5%, from about 1 to about 4%, from about 1 to about 3%, from about 1 to about 2%, from about 2 to about 19%, from about 3 to about 18%, from about 4 to about 17%, from about 5 to about 16%, from about 6 to about 15%, from about 7 to about 14%, from about 8 to about 13%, from about 9 to about 12%, from about 10 to about 11%, about 1%, about 2%, about 3%, about 4%, about 5%, about 6%, about 7%, about 8%, about 9%, about 10%, about 11%, about 12%, about 13%, about 14%, about 14%, about 15%, about 16%, about 18%, about 19%, or about 20% by weight of the metal nanoparticle in the colloidal suspension or dispersion.

The colloidal suspension or dispersion may also comprise bent-core liquid crystals. These are non-chiral compounds that can form chiral liquid crystalline phases due to their bent molecular structure and a molecular tilt within the layers of the layer structure resulting in a macroscopic polarization that can be switched between different orientations by applying an electric field.

The metal nanoparticles described herein which further comprise a luminescent atom or group may be used in self-illuminating displays.

The colloidal suspensions or dispersions described herein may be used in, for example, an optical device, an electro-optical device, a liquid crystal display, a liquid crystal thermometer, a coating, a sensor, an optical memory, a non-linear optical device, or a light shutter or valve.

EXAMPLES

The following examples are provided to illustrate the invention. It will be understood, however, that the specific details given in each example have been selected for the purpose of illustration and are not to be construed as limiting in scope of the invention.

General Considerations

HAuCl$_4$.3H$_2$O (99.999%), (S)-Naproxen, p-toluenesulfonic acid, NaBH$_4$, hexamethyldisilathiane (Me$_3$Si)$_2$S, hexan-1-thiol, dodecane-1-thiol, tetraoctylammonium bromide, 12-bromododencan-1-ol, and tetrabutylammonium fluoride TBAF (1.0M in THF) were purchased from Aldrich and used as received.

X-ray diffraction (XRD) patterns were obtained on an MPD X'Pert system (PANalytical) using CuK$_\alpha$ radiation (40 kv, 200 mA). Au3 and Au6 were measured in reflection geometry using a zero-background flat sample holder, Au7 using a 0.3 mm glass capillary in transmission geometry. UV-Vis spectra were obtained using an Agilent 8453 spectrophotometer. Transmission electron microscopy (TEM) images were obtained on a JEOL FX 2000 TEM instrument operating at an accelerating voltage of 160 kV. A 3 μL drop of the isolated gold colloid solutions was dropcasted on carbon coated cooper grids (400 mesh) and dried for 2 hours. Circular dichroism (CD) spectra were recorded on a J-810 spectropolarimeter (Jasco Inc.) using a bandwidth of 2 nm (accumulation of three spectra, circular quartz cuvettes with 1 cm path length). Polarizing optical microscopy (POM) was performed using an Olympus BX51-P polarizing microscope in conjunction with a Linkam LS350 heating/cooling stage.

Example 1

Synthesis of 12-sulfanyldodecyl (2S)-2-(6-methoxy-2-naphthyl)propanoate

First, 12-bromododecyl (2S)-2-(6-methoxy-2-naphthyl)propanoate was synthesized according to a procedure[33] using Naproxen (7.8 mmol, 1.8 g), 12-bromo-dodecan-1-ol (7.8 mmol, 2.0 g) and p-toluenesulfonic acid (9.8 mmol, 1.7 g) in toluene (50 ml). The mixture was refluxed for about 10 h under N$_2$ in a round bottom flask using a Dean-Stark trap. The reaction progress was monitored by TLC (hexane:ethyl acetate=8:2). After the reaction was complete, the reaction mixture was cooled to room temperature, and then washed with water (3×). The organic layer was separated, dried ($Na_2SO_4$), and the solvent evaporated under reduced pressure. The crude residue was purified by column chromatography (hexane:ethyl acetate=8:2) to afford 3.6 g (97%). $^1$H NMR (300 MHz, $CDCl_3$) δ (ppm): 1.22 (m, br, 16H, $CH_2$), 1.44 (m, H, $CH_2CH_2O$), 1.62 (d, 3H, J=7.2 Hz, $CH_3CH$), 1.88 (m, 2H, $CH_2CH_2Br$), 3.43 (t, 2H, J=6.8 Hz, $CH_2Br$), 3.83 (m, 1H, $CHCH_3$), 3.93 (s, 3H, $CH_3O$), 4.10 (t, 2H, J=6.6 Hz, $OCH_2CH_2$), 7.18 (m, 2H, Ar—H), 7.46 (d, 1H, J=8.5 Hz, Ar—H), 7.70 (d, 2H, J=3.6 Hz, Ar—H), 7.74 (s, 1H, Ar—H). $^{13}$C NMR (75 MHz, $CDCl_3$): 129.66, 128.63, 127.46, 126.31, 125.70, 119.32, 105.98, 65.28, 55.69, 45.95, 34.43, 33.25, 29.89, 29.17, 28.58, 26.19, 18.91. MS m/z (rel. int., %): 478 (7.1) [M]$^+$, 396 (9.3), 185 (100), 170 (5.9), 141 (7.5).

The compound 12-sulfanyldodecyl (2S)-2-(6-methoxy-2-naphthyl) propanoate was then synthesized according to a procedure reported by Hu and co-workers.[34] Briefly, 12-bromododecyl (2S)-2-(6-methoxy-2-naphthyl) propanoate (2.5 mmol, 1.2 g) was dissolved with freshly distilled dry THF (5 ml) and then cooled to −10° C. using an acetone/ice bath. To the resulting solution, hexamethyldisilathiane (3.0 mmol, 0.63 ml) and TBAF (1M in THF, 2.76 mmol, 2.76 ml) were added under an inert gas atmosphere. After the reaction was complete (TLC, hexane:ethyl acetate=8:2), the mixture was allowed to warm to room temperature. Thereafter, the solution was partitioned between diethyl ether (100 ml) and saturated aqueous ammonium chloride (100 ml), the layers were separated, and the organic phase washed with water (50 ml). After evaporation of the solvent under reduced pressure, the crude residue was purified by column chromatography (hexane:ethyl acetate=8:2) to yield 1.95 g of 12-sulfanyldodecyl (2S)-2-(6-methoxy-2-naphthyl) propanoate (60%). $^1$H NMR (300 MHz, $CDCl_3$) δ (ppm): 1.21-1.37 (m, br, 20H, $CH_2$, and overlapped 1H, SH), 1.58 (d, 3H, J=7.2 Hz, $CH_3CH$), 2.53 (q, 2H, J=7.5 Hz, $CH_2SH$), 3.88 (q, 1H, J=6.2 Hz, $CHCH_3$), 3.93 (s, 3H, $CH_3O$), 4.08 (t, 2H, J=6.8 Hz, $CH_2O$), 7.18 (m, 2H, Ar—H), 7.46 (d, 1H, J=1.8 Hz, Ar—H), 7.70 (d, 2H, J=4.4 Hz, Ar—H), 7.73 (s, 1H, Ar—H). $^{13}$C NMR (75 MHz, $CDCl_3$): 129.65, 127.45, 126.68, 126.30, 119.30, 105.97, 65.28, 55.68, 45.94, 34.45, 29.92, 29.47, 28.77, 26.31, 26.19, 25.05, 18.91. MS m/z (rel. int., %): 432 (3.4) [M]$^+$, 230 (3.2), 212 (5.3), 185 (100), 171 (2.7), 155 (2.0), 141 (8.8).

Example 2

Synthesis of Gold Nanoparticles

All glassware used for the preparation and storage of colloidal gold was treated with aqua regia, cleaned with piranha solution, and rinsed with deionized water (Millipore, resistivity 18.2 MΩ) and dried overnight at 100° C.

The gold nanoparticle Au3 was prepared according to the Brust procedure.[28] 12-sulfanyldodecyl (2S)-2-(6-methoxy-2-naphthyl) propanoate (1.16 mmol, 0.5 g) and $HAuCl_4.3H_2O$ (0.58 mmol, 0.2 g) were dissolved in freshly distilled dry THF (20 ml). The resulting solution was stirred 10 min, after which a freshly prepared solution of $NaBH_4$ (0.22 g) in deionized water (10 ml) was added at once. The mixture was stirred for additional 2 h. The solvent was evaporated under reduced pressure, and the black precipitate was collected and exhaustively washed with deionized water and hexane.

The gold nanoparticles Au1, Au2, Au4, Au5 and Au7 were also prepared according to the Brust procedure, while the gold nanoparticle Au6 was prepared according to the method by Shon and coworkers.[35]

Figure 3:
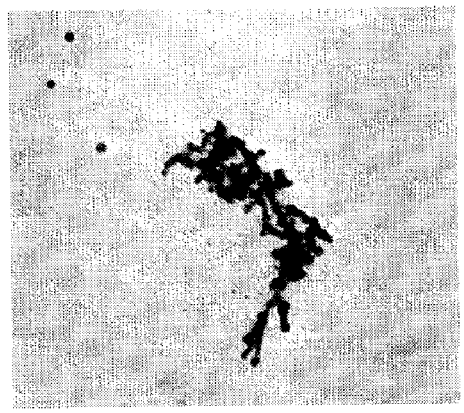
FIG. 3 is a Transmission Electron Microscopy (TEM) micrograph of Au3.
Figure 6:
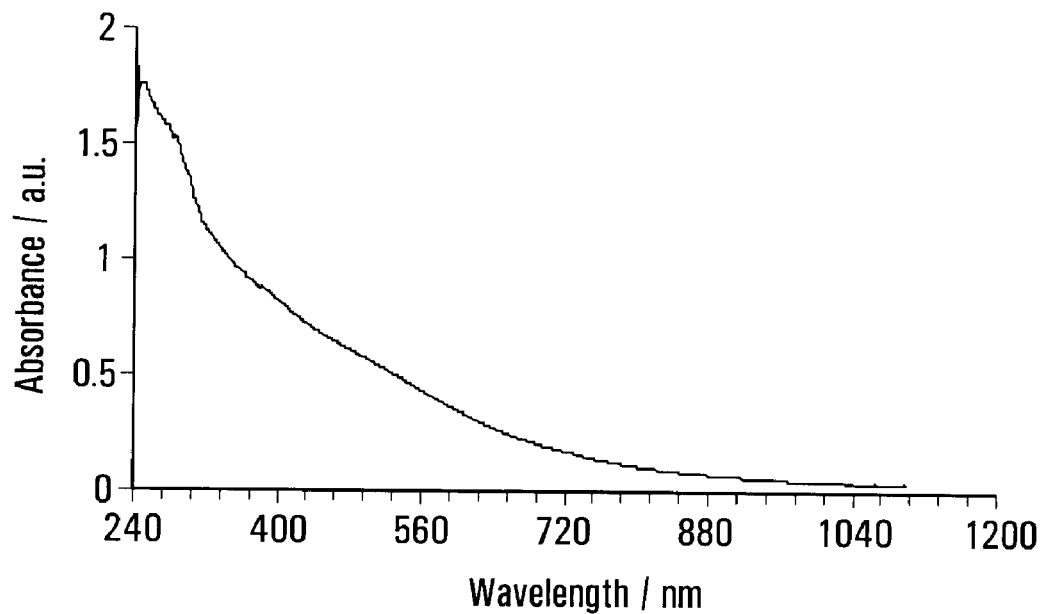
FIG. 6 is a UV-Vis spectrum of Au6.
Figure 7:
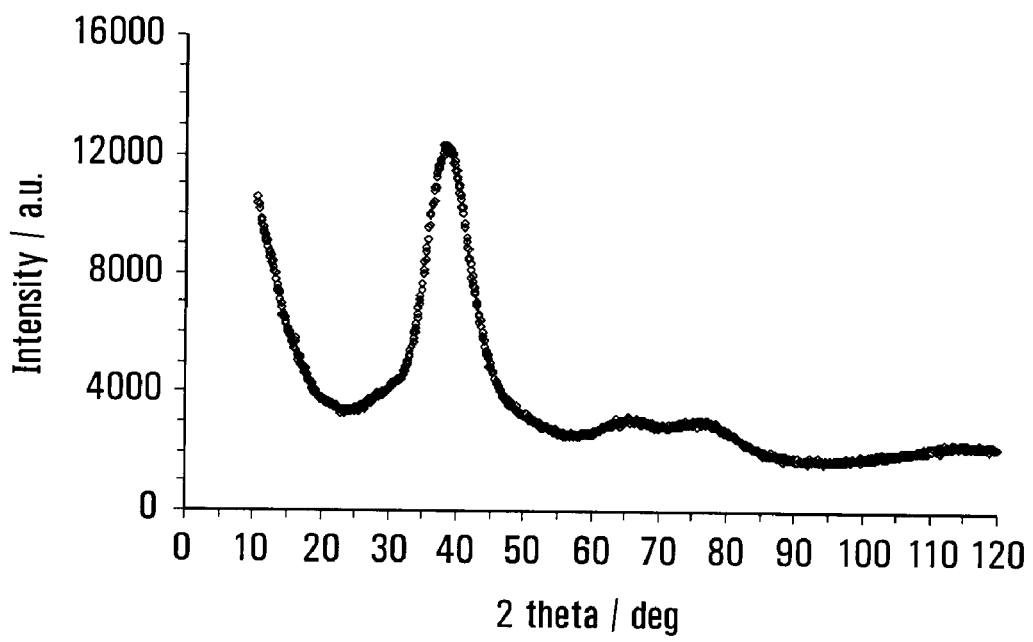
FIG. 7 is a XRD pattern of Au6.

The purity of each nanoparticle sample (removal of unreacted thiol) was checked by $^1$H NMR spectroscopy. Further, each nanoparticle sample was characterized by TEM (see representative examples in FIG. 3 to 5), UV-Vis (see representative example in FIG. 6) and XRD (see representative example in FIG. 7).

Figure 8:
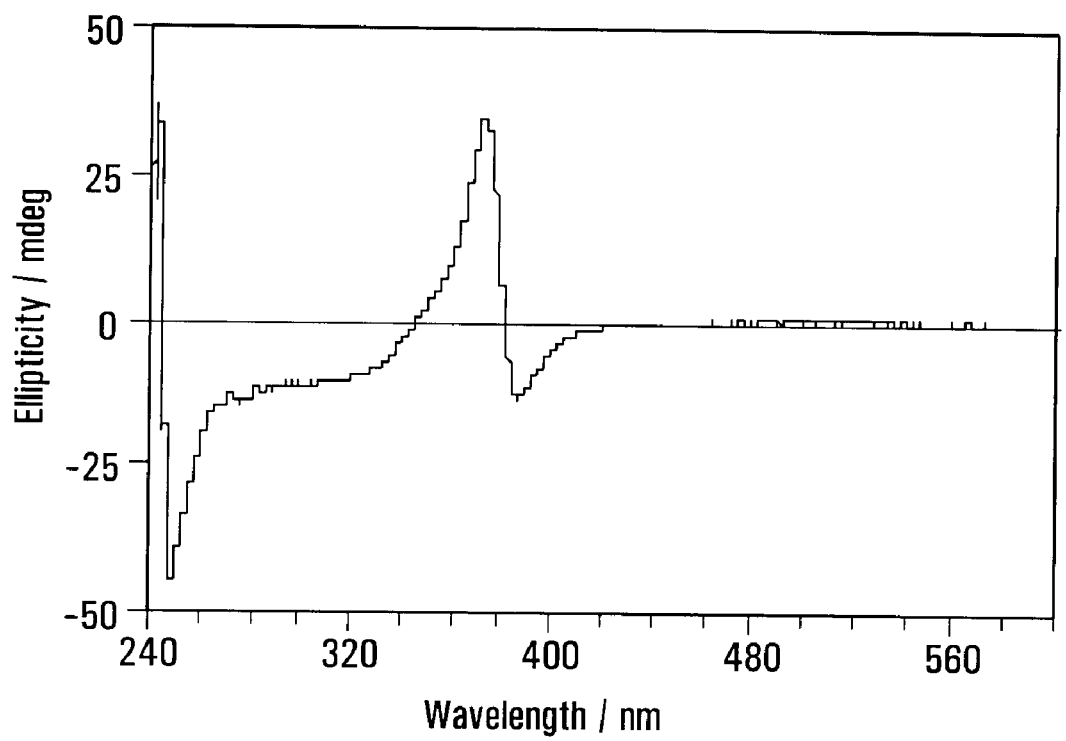
FIG. 8 is a Circular Dichroism (CD) spectrum of Au3.
Figure 9:
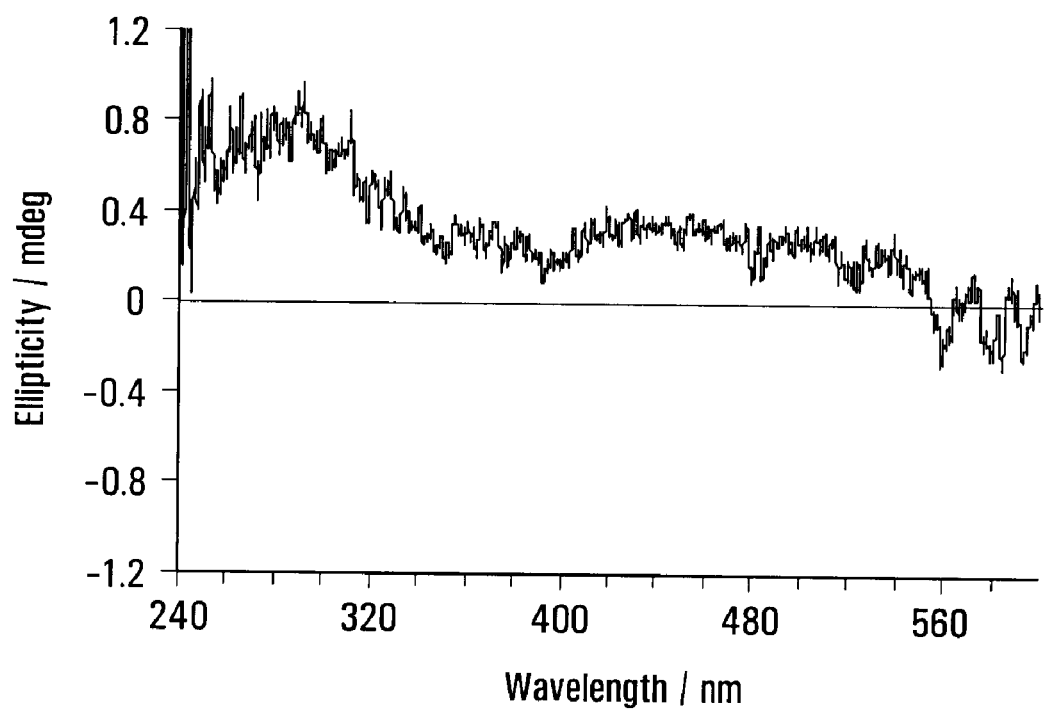
FIG. 9 is a CD spectrum of Au6.
Figure 10:
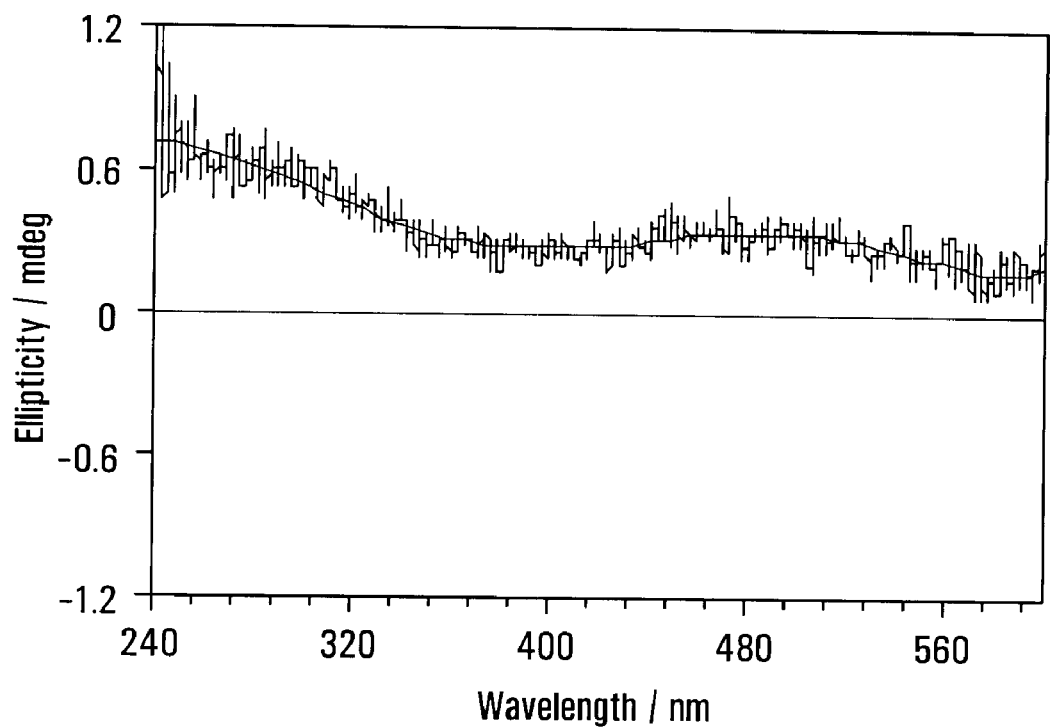
FIG. 10 is a CD spectrum of Au7.

To obtain information on the optical activity of the gold nanoparticles, the CD spectrum of each nanoparticle sample was measured in solution over a range extending from 240 to 600 nm (see representative example in FIG. 8 to 10).

Figure 4:
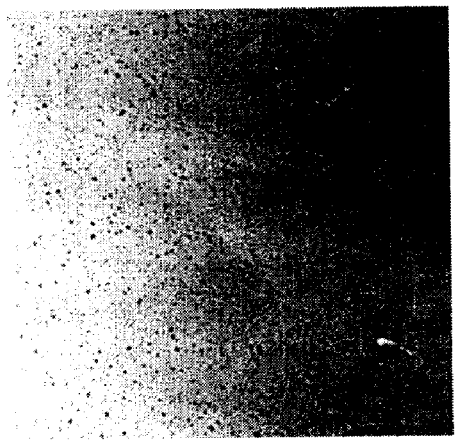
FIG. 4 is a TEM micrograph Au6.
Figure 5:
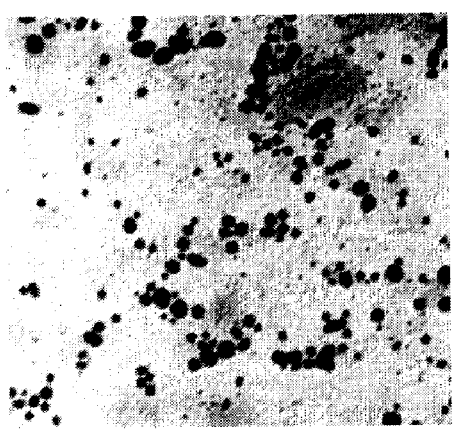
FIG. 5 is a TEM micrograph of Au7.

The CD spectra of hexane thiolate and dodecane thiolate protected gold nanoparticles exhibited weak CD signals with features centered at 285 and 475 nm that are attributed to scattering artifacts. The scattering observed for the ellipticity of the alkane thiolate clusters (Au6 and Au7) is also likely due to the size distribution of the present nanoparticles as observed by TEM (FIGS. 4 and 5). In contrast, the natural CD spectrum of the Naproxen functionalized gold nanoparticles (e.g., Au3) show well-defined Cotton effects centered at approximately 340 and 380 nm FIG. 8). Hence, all chirally-modified (with chiral dopant structures decorated) nanoparticle samples appear to be optically active.

Figure 11:
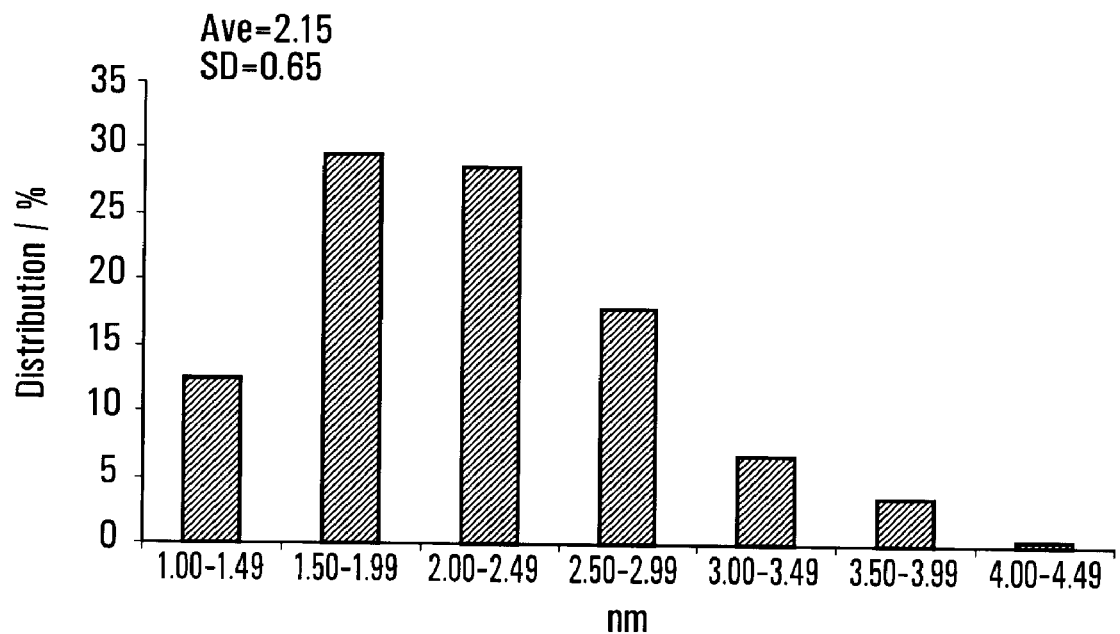
FIG. 11 is a graph showing a size-distribution analysis of Au6.

A representative example of a size distribution analysis of a gold nanoparticle is shown in FIG. 11. The average size of gold nanoclusters Au3, Au6 and Au7 was found to be 6.2, 1.3 and 5.9 nm (XRD), respectively.

Example 3

Liquid Crystal/Nanoparticle Mixtures

To probe the propensity of metal nanoparticles to induce chiral nematic phases upon dispersion in non-chiral nematic liquid crystal hosts, the gold nanoparticles Au1-Au7 were mixed with the nematic/monotropic smectic-C (SmC) liquid crystal Felix-2900-03.

All glass vials and Teflon-coated spatulas were rinsed with aqua regia prior to all mixtures preparations. Mixtures of Felix-2900-03 doped with Au1-Au7 were then prepared by mixing ready prepared solutions of both components in a common pure, dry solvent (e.g., ethyl acetate). The resulting solutions were sonicated for approximately 3 minutes, and the solvent was evaporated by a steady stream of dry $N_2$ over the open glass vials. Thereafter, all mixtures were dried in vacuum for 24 hours. Prior to the preparation of the thin films sandwiched between microscope glass slides, all mixtures were heated just below the isotropic-nematic phase transition ($T_{NI}$) and continuously mixed (stirred or sonicated).

Recent studies on the stability of thiolate-protected gold nanoparticles suggest that thiols with a carbon chain longer than $C_6$ begin to desorb from the gold nanoparticle surface above a threshold of 160° C.[36] Therefore, it was assumed that during all mixing experiments no changes in the nanoparticle composition (surface) via desorption of thiolate takes place.

Figure 12:
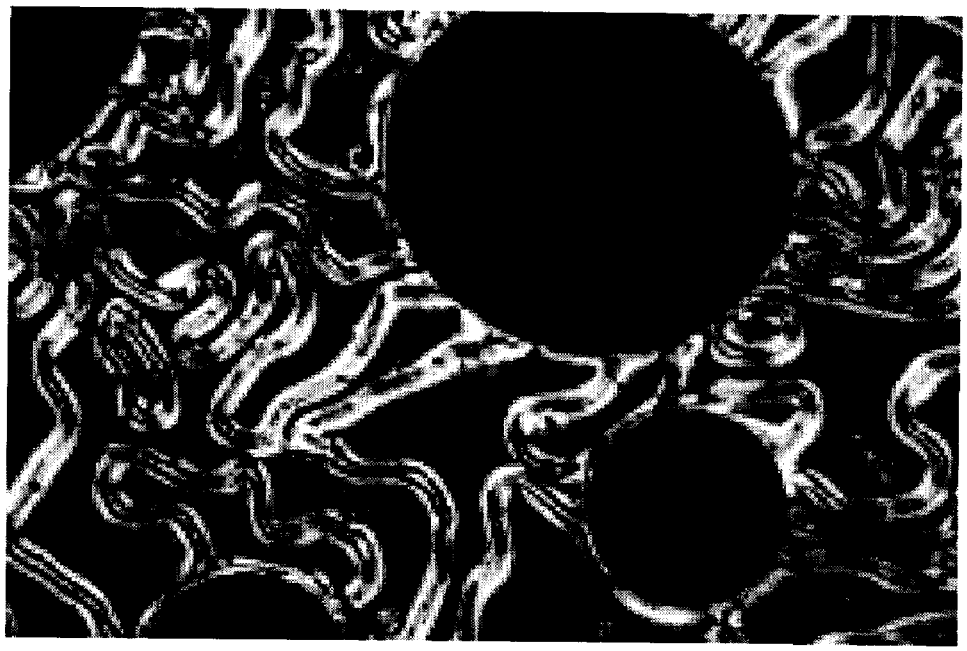
FIG. 12 is a POM micrograph (crossed polarizers) of the high temperature liquid crystal phase taken at 51° C. upon cooling from just below the isotropic-nematic phase transition showing the cholesteric finger-like texture and co-existing pseudo-isotropic areas of N* phase of Au3 in Felix-2900-03 (the large circular areas are air-bubbles in the LC film)
Figure 13:
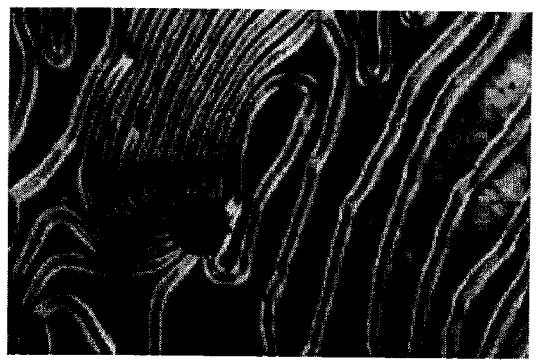
FIG. 13 is a POM micrograph (crossed polarizers) of the high temperature liquid crystal phase taken upon cooling from the isotropic-nematic phase transition at 64° C. showing the finger texture of N* phase of 5 wt % Au7 in Felix-2900-03.
Figure 14:
FIG. 14 is a POM micrograph (crossed polarizers) of the high temperature liquid crystal phase taken at 61° C. upon cooling from the isotropic-nematic phase transition showing the cholesteric finger-like texture and co-existing pseudo-isotropic areas of N* phase of 5 wt % Au7 in Felix-2900-03.

Rather striking is the effect of the thiolate-protected gold nanoparticles on the liquid crystal texture of the nematic phase of Felix-2900-03 as observed by Polarizing Optical Microscopy. On cooling from just below the nematic to isotropic phase transition ($T_{NI}$), Felix-2900-03 doped with 5 wt % of Au1-Au7 (see representative examples in FIGS. 12 to 14) showed the formation of finger textures similar to cholesteric finger textures non-chiral nematic liquid crystal doped a chiral dopant.

Figure 15:
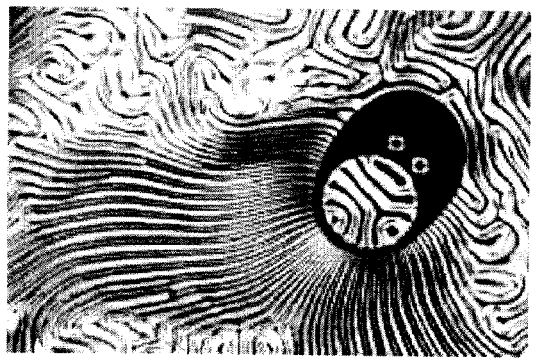
FIG. 15 is a POM micrograph (crossed polarizers) of the high temperature liquid crystal phase taken at 54° C. upon cooling from the isotropic-nematic phase transition showing the fingerprint texture of N* phase of Felix-2900-03 doped with 5 wt % of 12-sulfanyldodecyl (2S)-2-(6-methoxy-2-naphthyl)propanoate.
Figure 16:
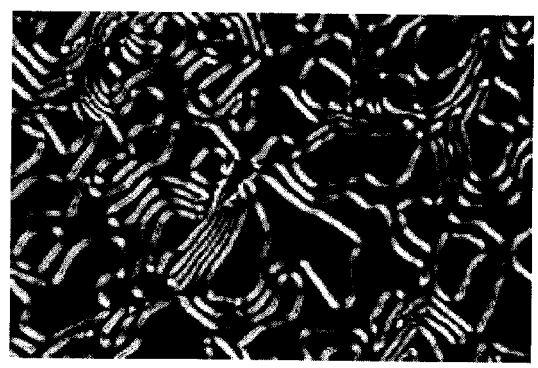
FIG. 16 is a POM micrograph (crossed polarizers) of the high temperature liquid crystal phase taken at 56° C. upon cooling from just below the isotropic-nematic phase transition showing the fingerprint texture of N* phase of Felix-2900-03 doped with 5 wt % of 12-sulfanyldodecyl (2S)-2-(6-methoxy-2-naphthyl)propanoate.
Figure 17:
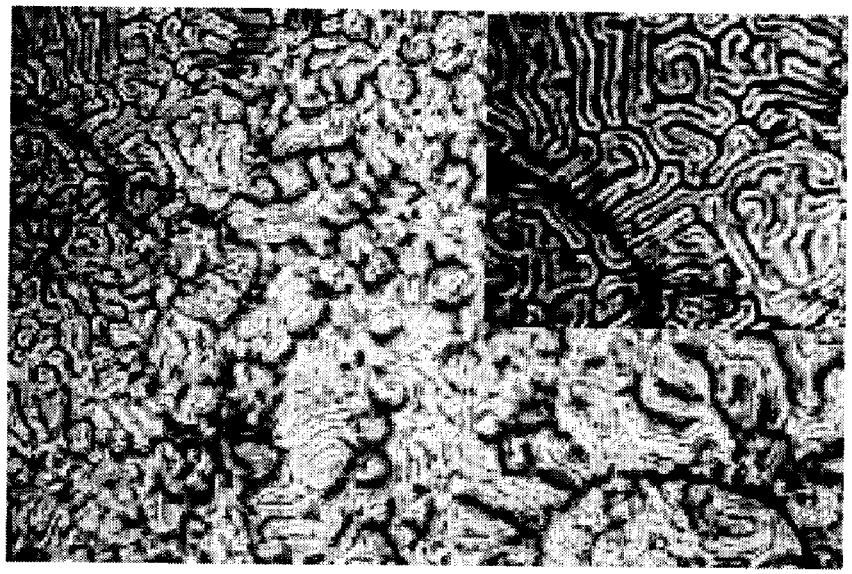
FIG. 17 is a POM micrograph (crossed polarizers) of the high temperature liquid crystal phase taken at 55° C. upon cooling from the isotropic-nematic phase transition showing the fingerprint texture of N* phase of 5 wt % Au7 in Felix-2900-03 doped with 5 wt % Naproxen (inset shows magnified area)
Figure 18:
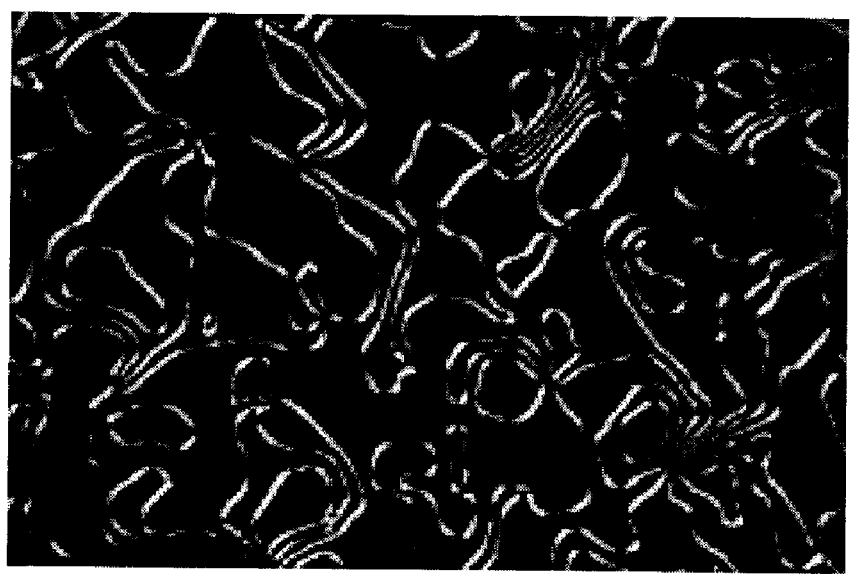
FIG. 18 is a POM micrograph (crossed polarizers) of the high temperature liquid crystal phase showing the texture of N* phase of 5 wt % Au7 in Felix-2900-03 in rubbed polyimide ITO glass cell (cell gap: 5 micron, no electric field is applied)

Similar chiral nematic textures were also observed for mixtures of Felix-2900-03 either doped with 5 wt % of the 12-sulfanyldodecyl (2S)-2-(6-methoxy-2-naphthyl) propanoate (FIGS. 15 and 16) or doped initially with 5 wt % Naproxen and then with 5 wt % Au7 (FIG. 17), as well as for a mixture of Felix-2900-03 doped with Au7 in rubbed polyimide glass cells (FIG. 18).

Figure 19:
FIG. 19 is a diagram showing polarized optical photomicrographs (crossed polarizers) of a nematic liquid crystal before and after doping with a metal nanoparticle, as a representative example of chirality transfer/chirality detection.
Figure 19:
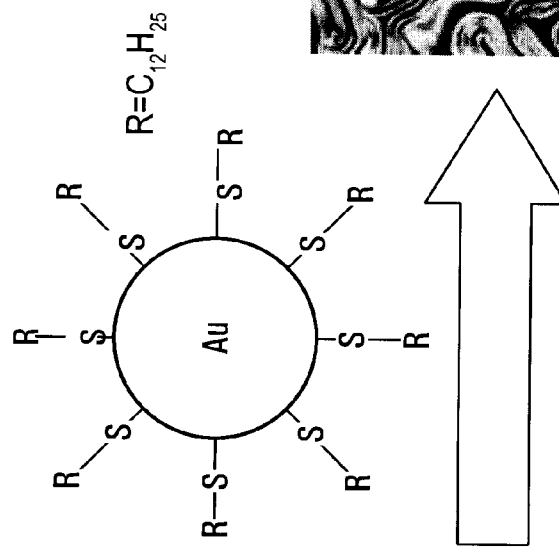
Figure 19:

A comparison of a nematic liquid crystal before and after doping with Au7 is shown in FIG. 19. There is a clear change to a texture after doping.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to".

REFERENCES

1. P. Poulin, H. Stark, T. C. Lubensky and D. A. Weitz, *Science*, 1997, 275, 1770.
2. O. V. Kuskenok, R. W. Rudwandl, S. V. Shiyanovskii and E. M. Terentjev, *Phys. Rev. E*, 1996, 54, 5198.
3. R. W. Ruhwandl and E. M. Terentjev, *Phys. Rev. E*, 1997, 56, 5561.
4. T. C. Lubensky, D. Pettey, N. Currier and H. Stark, *Phys. Rev. E*, 1998, 57, 610.
5. H. Stark, *Eur. Phys. J. B*, 1999, 10, 311.
6. H. Stark, J. Stelzer and R. Bernhard, *Eur. Phys. J. B*, 1999, 10, 515.
7. D. Andrienko, G. Germano and M. P. Allen, *Phys. Rev. E*, 2001, 63, 041701.
8. P. Poulin and D. A. Weitz, *Phys. Rev. E*, 1998, 57, 626.
9. O. Mondain-Monval, J. C. Dedieu, T. Gulik-Krzywicki and P. Poulin, *Eur. Phys. J. B*, 1999, 12, 167.
10. P. Poulin, V. Cabuil and D. A. Weitz, *Phys. Rev. Lett.*, 1997, 79, 4862.
11. J.-C. Loudet, P. Barois and P. Poulin, *Nature*, 2000, 407, 611.
12. J.-C. Loudet, P. Poulin and P. Barois, *Europhys. Lett.*, 2001, 54, 175.
13. J.-C. Loudet and P. Poulin, *Phys. Rev. Lett.*, 2001, 87, 165503.
14. J.-C. Loudet, O. Mondain-Monval and P. Poulin, *Eur. Phys. J. E*, 2002, 7, 205.
15. P. Poulin, N. France's and O. Mondain-Monval, *Phys. Rev. E*, 1999, 59, 4384.
16. Y. D. Gu and N. L. Abbott, *Phys. Rev. Lett.*, 2000, 85, 4719.
17. (a) J. Fukuda, H. Yokoyama, M. Yoneya and H. Stark, *Mol. Cryst. Liq. Cryst.*, 2005, 435, 723; (b) H. Stark, *Phys. Rev. E*, 2002, 66, 032701.
18. J. J. Feng and C. Zhou, *J. Colloid Interface Sci.*, 2004, 269, 72.
19. (a) M. Svetec, S. Kralj, Z. Bradač and S. Žumer, *Eur. Phys. J. E*, 2006, 20, 71; (b) P. Kossyrev, M. Ravnik and S. Žumer, *Phys. Rev. Lett.*, 2006, 96, 048301.
20. (a) Garzón, I. L.; Reyes-Nava, J. A.; Rodriguez-Hernández, J. I.; Sigal, I.; Beltrán, M. R.; Michaelian, K., *Phys. Rev. B*, 2002, 66, 073403; (b) Garzón, I. L.; Beltrán, M. R.; González, G.; Gutierrez-Gonzalez, I.; Michaelian, K.; Reyes-Nava, J. A.; Rodriguez-Hernández, J. I., *Eur. Phys. J. D*, 2003, 24, 105. (c) Román-Velázques, C. E.; Noguez, C.; Garzón, I. L., *J. Phys. Chem. B*, 2003, 107, 12035.
21. Schaaf, G. T.; Whetten, R. L., *J. Phys. Chem. B*, 2000, 104, 2630.
22. Buda, A. B.; Mislow, K., *J. Am. Chem. Soc.*, 1992, 114, 6006.
23. Coffey, L.; Drapala, J. A.; Erber, T., *J. Phys. A: Math. Gen.*, 1999, 32, 2263.
24. Tamura, M.; Fujihara, H., *J. Am. Chem. Soc.*, 2003, 125, 15742.
25. Yao, H.; Miki, K.; Nishida, N.; Sasaki, A.; Kimura, K., *J. Am. Chem. Soc.*, 2005, asap (ja053504b).
26. Friedel, G., *Ann. Phys. Paris*, 1922, 18, 273.
27. Dierking, I., *Textures of Liquid Crystals*; Wiley-VCH: Weinheim, 2003.
28. (a) Brust, M.; Walker, M.; Bethell, D.; Schiffrin, D. J.; Whyman, R., *J. Chem. Soc., Chem. Commun.*, 1994, 801. (b) Brust, M.; Fink, J.; Bethell, D.; Schiffrin, D. J.; Kiely, C., *J. Chem. Soc., Chem. Commun.*, 1995, 1655.
29. Vijaya Sarathy, K.; Raina, G.; Yadav, R. T.; Kulkarni, G. U.; Rao, C. N. R. *J. Phys. Chem. B*, 1997, 101, 9876-9880.
30. Kim, K.-S.; Demberelnyamba, D.; Huen, L. Langmuir, 2004, 20, 556-560.
31. dos Santos, Jr., D. S.; Alvarez-Puebla, R. A.; Oliveira, Jr., O. N.; Aroca, R. F. *J. Mater. Chem.*, 2005, 15, 3045-3049.
32. Templeton, A. C.; Wuelfing, W. P.; Murray, R. W. *Acc. Chem. Res.*, 2000, 33, 27-36.
33. Kazemekaite, M.; Bulovas, A.; Talalkyle, Z.; Butkus, E.; Railaite, V.; Niaura, G.; Palaima, A.; and Razumas, V., *Tetrahedron Letters*, 2004, 45, 3551.
34. Hu, J.; and Fox, M. A., *J. Org. Chem.*, 1999, 64, 4959.
35. Choo, H.; Cutler, E.; and Shon, Y. S., *Langmuir*, 2003, 19, 8555.
36. Büttner, M.; Belser, T.; and Oelhafen, P., *J. Phys. Chem. B*, 2005, 109, 5464.

The invention claimed is:

1. A metal nanoparticle comprising:
a metal; and
a chiral group bonded to the metal; and
a luminescent atom or group;
for use as a chiral dopant in a liquid crystal.

2. The metal nanoparticle according to claim 1, wherein the metal is gold, silver or platinum.

3. The metal nanoparticle according to claim 1, wherein the metal is gold.

4. The metal nanoparticle according to claim 1, wherein the chiral group is bonded to the metal through a thiol linkage.

5. The metal nanoparticle according to claim 4, wherein the thiol linkage comprises an aliphatic spacer.

6. The metal nanoparticle according to claim 5, wherein the aliphatic spacer is $C_{4-18}$ alkyl.

7. The metal nanoparticle according to claim 1, wherein the chiral group is a chiral ester.

8. The metal nanoparticle according to claim 1, wherein the average size of the metal nanoparticle is about 2 to about 5 nm.

9. The metal nanoparticle according to claim 1, further comprising an alkanethiol bonded to the metal.

10. The metal nanoparticle according to claim 1, wherein the luminescent atom or group is a lanthanide atom or an organic dye.

11. A metal nanoparticle of formula:

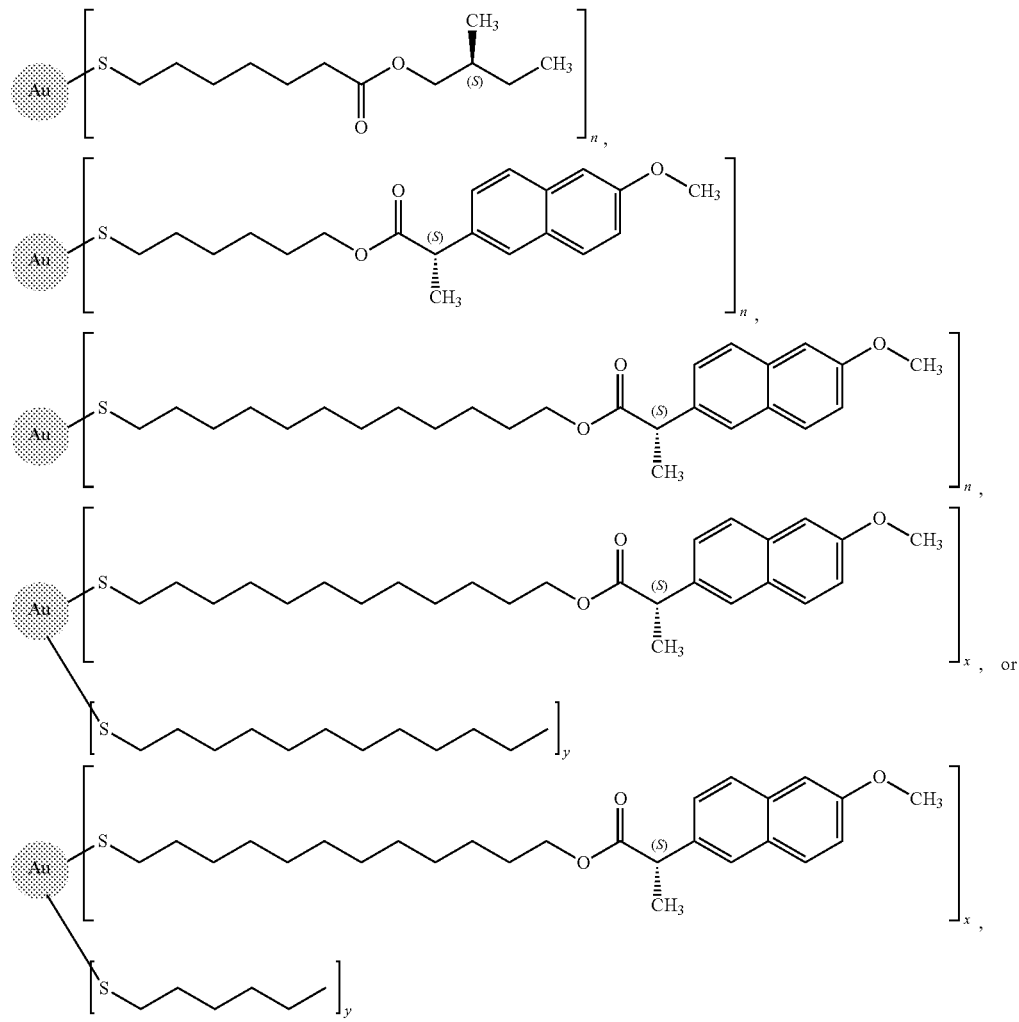

wherein n is greater than or equal to one, and x and y are in a ratio of about 5:1 to about 1:5.

12. The metal nanoparticle according to claim 1, wherein the liquid crystal is a non-chiral nematic liquid crystal or a smectic liquid crystal.

13. The metal nanoparticle according to claim 12, wherein the non-chiral nematic liquid crystal is uniaxial, biaxial, or discotic; and the smectic liquid crystal is smectic A, smectic C, or hexatic.

14. A colloidal suspension or dispersion comprising:
a metal nanoparticle comprising:
   a metal; and
   a chiral group bonded to the metal; and
a liquid crystal.

15. The colloidal suspension or dispersion according to claim 14, wherein the metal nanoparticle is in an amount less than 20 weight percent of the total colloidal suspension or dispersion.

16. The colloidal suspension or dispersion according to claim 14, wherein the liquid crystal is a non-chiral nematic liquid crystal or a smectic liquid crystal.

17. The colloidal suspension or dispersion according to claim 16, wherein the non-chiral nematic liquid crystal is uniaxial, biaxial, or discotic; and the smectic liquid crystal is smectic A, smectic C, or hexatic.

18. The colloidal suspension or dispersion according to claim 14, wherein the liquid crystal is

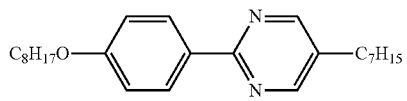

or a cyanobiphenyl derivative.

19. The colloidal suspension or dispersion according to claim 14 for use in an optical device, an electro-optical device, a liquid crystal display, a liquid crystal thermometer, a coating, a sensor, an optical memory, a non-linear optical device, or a light shutter or valve.

20. A process for preparing a metal nanoparticle comprising:
gold; and
a chiral group bonded to the gold; the process comprising:
   providing a solution comprising $HAuCl_4$ and a thiol comprising a chiral group, wherein the chiral group is a chiral ester; and reducing HAuCl$_4$ with a reducing agent to form the metal nanoparticle.

21. The process according to claim 20, wherein the thiol is 6-sulfanylhexyl (2S)-(6-methoxy-2-naphthyl)propanoate, 12-sulfanyldodecyl (2S)-(6-methoxy-2-naphthyl)propanoate, or (2S)-methylbutyl 7-sulfanylheptanoate.

22. The process according to claim 20, wherein the reducing agent is NaBH$_4$ or LiAlH$_4$.

23. The process according to claim 20, wherein the solution comprises tetrahydrofuran, toluene, hexane or a mixture thereof as a solvent.

24. A method comprising:
using a metal nanoparticle as a dopant in a liquid crystal, wherein the metal nanoparticle comprises:
a metal; and
a thiolate group bonded to the metal.

25. The method according to claim 24, wherein the metal is gold, silver or platinum.

26. The method according to claim 24, wherein the metal is gold.

27. The method according to claim 24, wherein the thiolate is chiral.

28. The method according to claim 24, wherein the thiolate is non-chiral.

29. The method according to claim 24, wherein the thiolate group is a C$_{4-18}$ alkanethiol optionally substituted with one or more of halogen, hydroxyl, carbonyl, thiocarbonyl, acyloxy, alkoxyl, phosphoryl, phosphonate, phosphinate, amino, acylamino, amido, amidine, amino, cyano, nitro, azido, sulfhydryl, alkylthio, sulfate, sulfonate, sulfamoyl, sulfonamido, heterocyclyl, aralkyl, an aromatic or heteroaromatic moiety.

30. The method according to claim 24, wherein the liquid crystal is a non-chiral nematic liquid crystal or a smectic liquid crystal.

31. The method according to claim 30, wherein the non-chiral nematic liquid crystal is uniaxial, biaxial, or discotic; and the smectic liquid crystal is smectic A, smectic C, or hexatic.

32. A colloidal suspension or dispersion comprising:
a metal nanoparticle comprising a metal and a thiolate group bonded to the metal; and
a liquid crystal.

33. The colloidal suspension or dispersion according to claim 32, wherein the metal nanoparticle is in an amount less than 20 weight percent of the total colloidal suspension or dispersion.

34. The colloidal suspension or dispersion according to claim 32, wherein the metal is gold, silver or platinum.

35. The colloidal suspension or dispersion according to claim 32, wherein the metal is gold.

36. The colloidal suspension or dispersion according to claim 32, wherein the thiolate is chiral.

37. The colloidal suspension or dispersion according to claim 32, wherein the thiolate is non-chiral.

38. The colloidal suspension or dispersion according to claim 32, wherein the thiolate group is a C$_{4-18}$ alkanethiol optionally substituted with one or more of halogen, hydroxyl, carbonyl, thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, an aromatic or heteroaromatic moiety.

39. The colloidal suspension or dispersion according to claim 32, wherein the average size of the metal nanoparticle is about 2 to about 5 nm.

40. The colloidal suspension or dispersion according to claim 32, wherein the metal nanoparticle further comprises a luminescent atom or group.

41. The colloidal suspension or dispersion according to claim 40, wherein the luminescent atom or group is a lanthanide atom or an organic dye.

42. The colloidal suspension or dispersion according to claim 32, wherein the metal nanoparticle is of formula:

[structure: Au—[S—(CH$_2$ chain)]$_n$, or Au—[S—(longer CH$_2$ chain)]$_n$]

wherein n is greater than or equal to one.

43. The colloidal suspension or dispersion according to claim 32, wherein the liquid crystal is a non-chiral nematic liquid crystal or a smectic liquid crystal.

44. The colloidal suspension or dispersion according to claim 43, wherein the non-chiral nematic liquid crystal is uniaxial, biaxial, or discotic; and the smectic liquid crystal is smectic A, smectic C, or hexatic.

45. The colloidal suspension or dispersion according to claim 32, wherein the liquid crystal is

[structure: C$_8$H$_{17}$O—phenyl—pyrimidine—C$_7$H$_{15}$]

or a cyanobiphenyl derivative.

46. The colloidal suspension or dispersion according to claim 32 for use in an optical device, an electro-optical device, a liquid crystal display, a liquid crystal thermometer, a coating, a sensor, an optical memory, a non-linear optical device, or a light shutter or valve.

47. A method for determining chirality or local chiral effects of a metal nanoparticle comprising:
mixing a non-chiral nematic liquid crystal with a metal nanoparticle; and
identifying a textural change in the non-chiral nematic liquid crystal to a nematic liquid crystal thin film showing birefringent stripe domains, colored when viewed with crossed polarizers as well as parallel polarizers,
wherein the presence of the textural change indicates a sort of chirality transfer or local induction of chiral interfaces by the metal nanoparticle.

48. A method for transferring chirality to a liquid crystal comprising:
providing a liquid crystal; and
doping the liquid crystal with a metal nanoparticle according to claim 1 comprising:
a metal; and
a chiral group bonded to the metal.

49. A method for transferring chirality to a liquid crystal comprising:
providing a liquid crystal; and
doping the liquid crystal with a metal nanoparticle comprising a metal and a thiolate group bonded to the metal.

50. A method for transferring chirality to a liquid crystal comprising:
providing a liquid crystal; and
doping the liquid crystal with a gold nanoparticle comprising gold and a thiolate group bonded to the gold.

51. The method according to claim 50, wherein the thiolate is chiral or non-chiral.

52. The metal nanoparticle according to claim 1, wherein the metal is palladium.

53. A metal nanoparticle comprising:
   a metal; and
   a chiral group bonded to the metal, wherein the chiral group is a chiral ester.

54. A liquid crystal cell comprising:
   a colloidal suspension or dispersion comprising:
      a metal; and
      a chiral group and/or a thiolate group bonded to the metal; and
   a glass cell;
wherein the metal is gold, silver, platinum, or palladium.

55. An electro-optical device comprising:
   a metal nanoparticle comprising:
      a metal; and
      a chiral group and/or a thiolate group bonded to the metal.

56. An electro-optical device according to claim 55, wherein the electro-optical device comprises a liquid crystal display.

57. The method according to claim 50, further comprising allowing chirality to transfer to the liquid crystal.

58. A method comprising:
   using a metal nanoparticle as a dopant in a liquid crystal, wherein the metal nanoparticle comprises:
      a metal; and
      a chiral group bonded to the metal.

* * * * *